United States Patent
Kawahara et al.

(10) Patent No.: US 6,292,532 B1
(45) Date of Patent: Sep. 18, 2001

(54) FLUORESCENT X-RAY ANALYZER USEABLE AS WAVELENGTH DISPERSIVE TYPE AND ENERGY DISPERSIVE TYPE

(75) Inventors: Naoki Kawahara; Takashi Shoji; Takashi Misonoo; Kouichi Aoyagi; Akira Arake; Takashi Sakamoto; Minoru Inoue; Yasujiro Yamada, all of Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 0 days.

(21) Appl. No.: 09/460,972

(22) Filed: Dec. 15, 1999

(30) Foreign Application Priority Data

Dec. 28, 1998 (JP) .................................... 10-374052
Dec. 28, 1998 (JP) .................................... 10-374053
Dec. 29, 1998 (JP) .................................... 10-377187

(51) Int. Cl.[7] ............................ G01N 23/223; G01T 1/36
(52) U.S. Cl. ................................. 378/49; 378/45; 378/46; 378/48; 378/50
(58) Field of Search ............................... 378/46, 6, 49; 250/269.2

(56) References Cited

U.S. PATENT DOCUMENTS 4,959,848 * 9/1990 Parobek .................... 378/46
4,988,872 * 1/1991 Nagatsuka et al. .................... 250/310

* cited by examiner

Primary Examiner—Robert H. Kim
(74) Attorney, Agent, or Firm—Sughrue, Mion, Zinn, Macpeak & Seas, PLLC

(57) ABSTRACT

A fluorescent X-ray analyzing apparatus capable of being used as either a wavelength dispersive type or an energy dispersive type is provided, with which the analysis can be performed quickly and accurately. The fluorescent X-ray analyzing apparatus includes a detecting unit for detecting and analyzing fluorescent X-ray (5) emitted from at least one target area (1*a*) of a sample (1) to be analyzed as a result of excitation of such target area (1*a*) with a primary X-ray (3). The detecting unit includes a wavelength dispersive type detecting unit (6) including a spectroscope (8) and a first detector (9), and an energy dispersive type detecting unit (11) including a second detector (12) of an energy dispersive type. The angle θ1 formed between a first path (81) of travel of the fluorescent X-ray from the target area (1*a*) towards the spectroscope (8) and a surface of the sample (1) is equal to the angle θ2 formed between a second path (82) of travel of the fluorescent X-ray from the target area (1*a*) towards the second detector (12) of the energy dispersive type and a surface of the sample (1), but the second path (82) is shorter than the first path (81).

15 Claims, 15 Drawing Sheets

FLUORESCENT X-RAY ANALYZER USEABLE AS WAVELENGTH DISPERSIVE TYPE AND ENERGY DISPERSIVE TYPE

BACKGROUND OF THE INVENTION

1. Field of the Invention

The present invention generally relates to a fluorescent X-ray analyzing apparatus and, more particularly, to the fluorescent X-ray analyzing apparatus capable of being used selectively as a wavelength dispersive type and an energy dispersive type.

2. Description of the Prior Art

The fluorescent X-ray analyzing apparatus is well known as an instrument for analyzing elements contained in an area of interest of a sample by applying primary X-rays to such area interest to excite the target area and subsequently detecting, by means of a detecting means, fluorescent X-rays emitted from the area of interest as a result of excitation thereof. The detecting means are currently available in two types; wavelength dispersive type and energy dispersive type. The area of interest of the sample referred to hereinabove and hereinafter is intended to encompass at least a portion of a surface of the sample at an arbitrary site on the sample and its nearby deep structure. At least a portion of the sample surface referred to above is to be understood as including the entire surface of the sample.

The wavelength dispersive type detecting means although having an excellent wavelength resolving power characteristically recurs a relatively large length time to measure the intensity of the fluorescent X-rays. On the other hand, the energy dispersive type detecting means has a wavelength resolving power less than that exhibited by the wavelength dispersive type detecting means, but has a feature in that intensities of the fluorescent X-rays over a broad range of wavelengths can be simultaneously measured. Accordingly, where broad wavelength distribution characteristics are desired to be examined in a short length of time, the energy dispersive type detecting means can be advantageously utilized therefore, but where a precise fluorescent X-ray analysis, that is, a high-resolution fluorescent X-ray analysis over a relatively narrow range of wavelength is desired to be performed, the wavelength dispersive type detecting means can be advantageously utilized therefore. Thus, if the energy dispersive type detecting means and the wavelength dispersive type detecting means are used one at a time depending on the purpose of analysis, the efficient analysis can be done. Also, if a qualitative analysis is carried out by the use of the energy dispersive type detecting means and the subsequent qualitative analysis of elements of interest is carried out by the use of the wavelength dispersive type detecting means, a quick and accurate fluorescent X-ray analysis can be performed with respect to totally unknown samples.

An X-ray analyzing apparatus employing both the wavelength dispersive type detecting means and the energy dispersive type detecting means for detecting the X-rays has been well known in the art. By way of example, the X-ray analyzing apparatus disclosed in the Japanese Laid-open Patent Publication No. 5-281163 includes, as shown in FIG. 16, an X-ray tube 4 for radiating primary X-rays 3 towards a sample 1 supported on a sample support 2 to excite the sample 1, a divergent Soller slit for collimating secondary X-rays 5 emitted from the sample 1 as a result of excitation thereof, a spectroscope 8 for analyzing the collimated secondary X-rays which is subsequently detected by a detector 9. The X-ray analyzing apparatus disclosed in the above mentioned publication and shown in FIG. 16 makes use of an energy dispersive type detector 12 for detecting the secondary X-rays 5 emitted from the sample 1.

The Japanese Laid-open Patent Publication No. 10-206356 discloses such a fluorescent X-ray analyzing apparatus as shown in FIG. 17. The fluorescent X-ray analyzing apparatus shown in FIG. 17 is so designed and so configured that the fluorescent X-rays 5 emitted from the sample 1 on the sample support 2 when the sample 1 is excited by the primary X-rays 3 emitted from the X-ray tube 4 can be detected by the detector 9 after having passed through the spectroscope 8. The spectroscope 8 used therein is supported for movement between an operative position, in which as shown by the solid line in FIG. 17 the spectroscope 8 is aligned with the path of travel of the fluorescent X-rays 5, and a retracted position in which the spectroscope 8 having been moved in a direction shown by the arrow A is retracted from the path of travel of the fluorescent X-ray 5.

Accordingly, when the spectroscope 8 is moved to the retracted position, the energy dispersive type detector 12 is brought in position to detect the fluorescent X-rays 5.

However, in the case of the X-ray analyzing apparatus shown in FIG. 16, the angle between the first path of travel 81 of the fluorescent X-rays, extending between the sample 1 and the spectroscope 8, and the surface of the sample 1, that is, the angle $\theta1$ of emergence of the fluorescent X-rays 5 to be detected by the wavelength dispersive type detector 9 differs from the angle between the second path of travel 82 of the fluorescent X-rays, extending between the sample 1 and the energy dispersive type detector 12, and the surface of the sample 1, that is, the angle $\theta2$ of emergence of the fluorescent X-rays 5 to be detected by the energy dispersive type detector 12. In other words, in order to enhance the strength of the energy dispersive type detector 12 as high as possible while because the energy dispersive type detector 12 has a small light receiving area the intensity of the fluorescent X-rays incident upon the energy dispersive type detector 12 tends to be low, the angle of emergence of the fluorescent X-rays to be detected by the energy dispersive type detector 12 is chosen to be large.

On the other hand, in the X-ray analysis, the intensity of X-rays to be measured depends on the angle of emergence and the correlation therebetween is complicated. Accordingly, where the angle $\theta1$ of emergence for the wavelength dispersive type detector and the angle $\theta2$ of emergence for the energy dispersive type detector are different from each other as discussed above, the intensity of the fluorescent X-rays measured by the wavelength dispersive type detector and that by the energy dispersive type detector cannot be correlated with each other. Moreover, even though compensation for the difference in angle of emergence is made, the correlation between the X-ray intensities with respect to the angle of emergence depends also on the composition of the sample and is thus complicated. Therefore, the compensation cannot be made accurately and, because of this uncertainty, the analyzing accuracy cannot be increased.

Also, if the sample has a rough surface full of minute surface irregularities, distribution characteristics of the X-ray wavelengths vary even though the angles of emergence are equal to each other when the spectroscope and the detector aim at the same area of interest of the sample from different directions, resulting in respective results of measurement which cannot be correlated with each other unless modified in any way.

In contrast thereto, in the case of the fluorescent X-ray analyzing apparatus shown in FIG. 17, the first path of travel 81 of the fluorescent X-rays and the second path of travel 82 of the fluorescent X-rays lie on the same path and the angle of emergence for the energy dispersive type detector and the angle of emergence for the wavelength dispersive type detector remain the same at the angle θ1. Accordingly, the intensity of the X-rays detected by the energy dispersive type detector and that by the wavelength dispersive type detector can be correlated with each other if they are multiplied by a predetermined sensitivity coefficient peculiar to the respective detecting system that does not depend on the sample.

However, since the energy dispersive type detector generally has a small light receiving area such as observed in a semiconductor detector (SSD) having a relatively excellent energy resolving power, the sensitivity will lower unless the energy dispersive type detector 12 is positioned close to the sample 1. Although in the fluorescent X-ray analyzing apparatus equipped with only the energy dispersive type detector the energy dispersive type detector can be positioned close to the sample 1 since no spectroscope is employed therein, the energy dispersive type detector 12 employed in the fluorescent X-ray analyzing apparatus shown in FIG. 17 cannot be positioned close to the sample 1 since in the fluorescent X-ray analyzing apparatus of FIG. 17 the spectroscope 8 is disposed between the sample 1 and the energy dispersive type detector 12. Accordingly, during detection by the use of the energy dispersive type detector, the sensitivity tends to lower and, particularly where the fluorescent X-rays emitted from a minute area of the sample are desired to be detected, no sufficient sensitivity required for the analysis cannot be secured.

Also, the conventional fluorescent X-ray analyzing apparatus that can be used as the wavelength dispersive type and the wavelength dispersive type one at a time has the following problem. In order to increase the accuracy of the quantitative analysis and the qualitative analysis, a so-called semiquantitative analysis is generally carried out prior to the analysis to determine varieties of and approximate contents of elements of interest contained in the sample. Unless respective results of detection given by the wavelength dispersive type detecting means and the energy dispersive type detecting means during the semiquantitative analysis are properly combined and used, neither the qualitative analysis nor the quantitative analysis can be performed quickly and accurately.

As hereinabove discussed, according to the prior art, the fluorescent X-ray analyzing apparatus that can be used as either a wavelength dispersive type or an energy dispersive type is incapable of performing a quick and accurate analysis.

SUMMARY OF THE INVENTION

Accordingly, the present invention is intended to provide an improved fluorescent X-ray analyzing apparatus of a kind capable of being used as either a wavelength dispersive type or an energy dispersive type, with which the analysis can be performed quickly and accurately.

To this end, the present invention provides a fluorescent X-ray analyzing apparatus which comprises a detecting means for detecting and analyzing, by means of a detecting means, fluorescent X-ray emitted from at least one predetermined target area of a sample to be analyzed as a result of excitation of such target area with a primary X-ray. The detecting means comprises a wavelength dispersive type detecting means including a spectroscope and a first detector, and an energy dispersive type detecting means including a second detector of an energy dispersive type. The angle formed between a first path of travel of the fluorescent X-ray from the target area towards the spectroscope and a surface of the sample is equal to an angle formed between a second path of travel of the fluorescent X-ray from the target area towards the second detector of the energy dispersive type and a surface of the sample, but the second path of travel of the fluorescent X-ray is shorter than the first path of travel of the fluorescent X-ray.

With this structure, since the angle of emergence for the wavelength dispersive type is equal to the angle of emergence for the energy dispersive type, the respective intensities of the fluorescent X-ray measured can be correlated with each other in the form as presented if each of those intensities is multiplied by a predetermined sensitivity coefficient peculiar to the respective detecting system that does not depend on the sample. Accordingly, the uncertainty resulting from the complicated correlation of the fluorescent X-ray relative to the angle of emergence can be suppressed, accompanied by increase in analyzing accuracy. Also, since the second detector of the energy dispersive type is positioned closer to the sample than the spectroscope, the second detector can be positioned at a location closer to the sample 1. Therefore, even in the case where the fluorescent X-ray from the very minute target area of the sample is measured, a sufficient sensitivity can be secured as is the case with the analyzing apparatus equipped with only the energy dispersive type detecting means and without the wavelength dispersive type detecting means, resulting in increase of the analytical accuracy. In other words, in the fluorescent X-ray analyzing apparatus capable of being used as both the wavelength dispersive type and the energy dispersive type, a quick and accurate analysis can be achieved.

Preferably, the fluorescent X-ray analyzing apparatus further comprises a detector drive mechanism for selectively advancing and retracting the second detector of the energy dispersive type into and out of alignment with the first path of travel of the fluorescent X-ray, whereby when the second detector of the energy dispersive type is advanced by such detector drive mechanism, the first and second paths of travel of the fluorescent X-ray lie on the same axis. With this structure, even though the sample has a rough surface full of minute surface irregularities, since the first path of travel of the fluorescent X-ray and the second path of travel of the fluorescent X-ray lie on the same axis, the second detector of the energy dispersive type and the spectroscope of the wavelength dispersive type are aligned with the target area 1a of the sample 1 from the same direction and, therefore, no deviation occur in respective results of measurement and the respective results of measurement can be correlated with each other in the form as presented after they have been multiplied by a predetermined sensitive coefficient that does not depend on the type of the sample and that is peculiar to the respective detection system. Also, since the second detector of the energy dispersive type can be selectively moved into and retracted from the path of travel of the fluorescent X-ray between the spectroscope and the sample, the second detector can be held at a position closer to the sample 1 when the second detector is moved into the path of travel of the fluorescent X-ray, ensuring a sufficient sensitivity and increase in analytical accuracy as is the case with the analyzing apparatus equipped with only the energy dispersive type detecting means and without the wavelength dispersive type detecting means.

Also preferably the fluorescent X-ray analyzing apparatus further comprises a first collimator positioned between the second detector of the energy dispersive type and the sample and having at least one throttling aperture defined therein for passage of the fluorescent X-ray therethrough, wherefore the fluorescent X-ray passing through the throttling aperture in the first collimator can be detected by the second detector of the energy dispersive type or detected by the first detector after having been analyzed by the spectroscope. According to this feature, since the throttle aperture of the first collimator is concurrently utilized by the energy dispersive type detecting means and the wavelength dispersive type detecting means, the same target area of the sample can be analyzed by both the energy dispersive type detecting means and the wavelength dispersive type detecting means. Accordingly, after the wavelength distribution characteristic of the fluorescent X-ray of a considerably low intensity from the minute target area of the sample has been examined in a short length of time by the energy dispersive type detecting means, the intensity of the fluorescent X-ray in the required wavelength range thereof can be measured by the wavelength dispersive type detecting means having a high resolving power and, therefore, the analysis of the minute target area of the sample can be performed quickly and accurately.

The fluorescent X-ray analyzing apparatus may additionally include a second collimator disposed between the first collimator and the spectroscope and having at least one throttle aperture defined therein, and wherein said second detector of the energy dispersive type is fitted to the second collimator. According to this feature, if the throttling aperture of the second collimator is positioned n the first path of travel of the fluorescent X-ray between the sample and the spectroscope, the second collimator serves as a field limiting aperture. On the other hand, if the second detector fitted to the second collimator is positioned on the first path of travel of the fluorescent X-ray between the sample and the spectroscope, the second collimator serves as a support member for the support of the second detector. In addition, since the second collimator is drivingly coupled with a detector drive mechanism for advancing and retracting the second detector of the energy dispersive type into and out of the path of travel of the fluorescent X-ray, the throttling aperture of the second collimator is also moved to the first path of travel of the fluorescent X-ray by this detector drive mechanism and, even where the second collimator has a plurality of throttling apertures defined therein, switching from one throttling aperture over to another can easily be accomplished.

Where the fluorescent X-ray analyzing apparatus includes a sample drive mechanism for moving the target area of the sample placed on a sample support, it is possible to allow the primary X-ray to radiate the target area, which is an arbitrarily chosen site of the sample, at all times on a predetermined intensity distribution by the sample drive mechanism. Accordingly, a quick and accurate analysis of the minute target area of the sample can be easily performed with respect to the arbitrarily chosen site of the sample.

The spectroscope is preferably a double crystal spectroscope including two spectroscopic crystals positioned fore and aft along the path of travel of the fluorescent X-ray. This features permits an analysis of a chemical condition by means of the wavelength dispersive type detector after the qualitative analysis by means of the energy dispersive type detector. In such case, as compared with the qualitative analysis with the use of the wavelength dispersive type detector of a kind comprising a one crystal spectroscope, the length of time required to switch from the qualitative analysis over to the analysis of the chemical condition can be shortened and convenient.

In a preferred embodiment of the present invention, the fluorescent X-ray analyzing apparatus further comprises a first collimator positioned between the second detector of the energy dispersive type and the sample and having at least one throttling aperture defined therein for passage of the fluorescent X-ray therethrough, wherefore the fluorescent X-ray passing through the throttling aperture in the first collimator can be detected by the second detector of the energy dispersive type or detected by the first detector after having been analyzed by the spectroscope; a sample drive mechanism for moving the target area of the sample placed on a sample support; imaging means of imaging the surface of the sample to form a sample image; display means for displaying the sample image formed by the imaging means; and control means for controlling the sample drive mechanism so as to allow the fluorescent X-ray, emitted from a site of the sample, specified with reference to the sample image displayed by the display means, to be incident upon any of the wavelength dispersive type detecting means and the energy dispersive type detecting means.

According to this structure, since the arbitrarily chosen minute site can be specified while looking at the image formed directly of the surface of the sample, the arbitrarily chosen minute target area of the sample can be quickly and accurately determined. Also, with respect to the fluorescent X-ray of a very low intensity from the minute target area, the field of which has been limited by the first collimator, after the wavelength distribution characteristic has been examined in a short length of time with the use of the energy dispersive detecting means of a high sensitivity, the intensity thereof can be measured over the required wavelength range with the use of the wavelength dispersive type detecting means of a high resolving power, thus making it possible to accomplish a quick and accurate analysis of the determined minute target area. Accordingly, the arbitrarily chosen minute site of the sample can be quickly and accurately analyzed. The fluorescent X-ray analyzing apparatus wherein said imaging means images the surface of the sample placed on the sample support to form the sample image. This feature makes it possible to specify the arbitrarily chosen site of the sample while looking at the image formed directly of the surface of the sample placed on the sample support just before the measurement and, therefore, the arbitrarily chosen minute target area of the sample can be further accurately determined.

The wavelength dispersive type detecting means preferably includes a Soller slit, and said Soller slit and at least a portion of the imaging means are positioned between the first collimator and the spectroscope. In such case, the fluorescent X-ray analyzing apparatus may further comprise a selector means for bringing one of them selectively to a position confronting the sample placed on the sample support. According to this feature, since the selector means for moving the imaging means concurrently serves as a changer for changing the Soller slit, the analyzing apparatus can be easily constructed.

In a preferred embodiment of the present invention, the first collimator is employed, and the fluorescent X-ray passing through at least one of throttling apertures of the first collimator is detected by the second detector of the energy dispersive type or by the first detector after having been analyzed by the spectroscope. The second collimator is also employed, to which the second detector of the energy dispersive type is fitted to the second collimator. The fluorescent X-ray analyzing apparatus may further comprise a sample drive mechanism for moving the target area of sample placed on a sample support; imaging means of imaging the surface of the sample to form a sample image; display means for displaying the sample image formed by the imaging means; and control means for controlling the sample drive mechanism so as to allow the fluorescent X-ray, emitted from a site of the sample, specified with reference to the sample image displayed by the display means, to be incident upon any of the wavelength dispersive type detecting means and the energy dispersive type detecting means.

Even with this structure, since the arbitrarily chosen site of the sample can be specified while looking at the image formed directly of the surface of the sample, the arbitrarily minute target area of the sample can quickly and accurately be determined. Also, with respect to the fluorescent X-ray of a very low intensity from the minute target area, the field of which has been limited by the first collimator, after the wavelength distribution characteristic has been examined in a short length of time with the use of the energy dispersive detecting means of a high sensitivity, the intensity thereof can be measured over the required wavelength range with the use of the wavelength dispersive type detecting means of a high resolving power, thus making it possible to accomplish a quick and accurate analysis of the determined minute target area. Accordingly, the arbitrarily chosen minute site of the sample can be quickly and accurately analyzed. The imaging means can image the surface of the sample placed on the sample support to form the sample image. According to this feature, it is possible to specify the arbitrarily chosen site of the sample while looking at the image formed directly of the surface of the sample placed on the sample support just before the measurement and, therefore, the arbitrarily chosen minute target area of the sample can be further accurately determined.

The wavelength dispersive type detecting means preferably includes a Soller slit, and the Soller slit and at least a portion of the imaging means are positioned between the first collimator and the spectroscope. A selector means is utilized in this arrangement for bringing one of them selectively to a position confronting the sample placed on the sample support. In such case, the fluorescent X-ray analyzing apparatus may further comprise a selector means for bringing one of them selectively to a position confronting the sample placed on the sample support. According to this feature, since the selector means for moving the imaging means concurrently serves as a changer for changing the Soller slit, the analyzing apparatus can be easily constructed.

In an alternative embodiment of the present invention, there is provided a fluorescent X-ray analyzing apparatus which comprises detecting means for detecting and analyzing, by means of a detecting means, fluorescent X-ray emitted from at least one predetermined target area of a sample to be analyzed as a result of excitation of such target area with a primary X-ray. The detecting means comprises a wavelength dispersive type detecting means including a spectroscope and a first detector, and an energy dispersive type detecting means including a second detector of an energy dispersive type. The analyzing apparatus furthermore includes a first measurement control means for obtaining a first result of measurement by causing the wavelength dispersive type detecting means to measure mainly an intensity of fluorescent X-rays in a region of a light element and also causing the energy dispersive type detecting means to measure mainly an intensity of fluorescent X-rays in a region of a heavy element; and an analytical data processing means for performing at least one of qualitative analysis, semiquantitative analysis and quantitative analysis of the sample based on the first result of measurement.

The wavelength dispersive type detecting means is generally used to measure the intensity of the fluorescent X-ray mainly in a region of light elements, but may be often used to measure that in a region of a small number of heavy elements. By way of example, in the case of measurement of a small quantity of arsenic, lead and so on which are heavy element contained in industrial waste containing, for example, a large amount of copper, iron, zinc and so on, spectra of copper, iron, zinc and so on tend to overlap and, therefore, the energy dispersive type detecting means having a low resolving power is incapable of performing measurement with respect to arsenic, lead and so on and the wavelength dispersive type detecting means is generally utilized for this purpose.

On the other hand, the energy dispersive type detecting means is generally used to measure the intensity of the fluorescent X-ray mainly in a region of heavy elements, but may be often used to measure that in a region of a small number of light elements. By way of example, in the case of the sample containing, as a principal component, a light element, for example, silica, alumina and so on such as, for example, soil and rocks, the energy dispersive type detecting means is effectively used for the measurement since the length of time required to accomplish the analysis can be shortened.

The semiquantitative analysis includes (1) a quantitative analysis of a small number of elements, (2) a quantitative analysis using calibration curves prepared from a small number, for example, two standard samples, and (3) a quantitative analysis using rough data of qualitative analysis. Respective results of the qualitative analysis and the semiquantitative analysis may be combined.

According to this structure, mainly the region of the light element can be accurately measured by the wavelength dispersive type detecting means with high detection accuracy whereas mainly the region of the heavy element can be measured by the energy dispersive type detecting means in a short length of time. Accordingly, the qualitative and quantitative analysis of the sample can be performed highly accurately in a short length of time. In other words, with the fluorescent X-ray analyzing apparatus that can be used either as the wavelength dispersive type or the energy dispersive type, a quick and accurate analysis is possible.

Preferably, the fluorescent X-ray analyzing apparatus further comprises a priority means for preferentially utilizing a result of measurement by the energy dispersive type detecting means as the first result of measurement in the event that a spectrum measured by the wavelength dispersive type detecting means contain an overlap of high-order lines. This feature is advantageous in that should measurement be difficult to accomplish because the result of measurement done by the wavelength dispersive type detecting means contains an overlap with high-order lines, the energy dispersive type detecting means does not measure the high-order line and, therefore, by preferentially choosing this result of measurement, the qualitative and quantitative analysis of the sample can be performed highly accurately.

Again preferably, the fluorescent X-ray analyzing apparatus further comprises a group selecting means for selecting a group to which the sample belongs, from a result of one of the qualitative analysis and the semiquantitative analysis of the sample determined by the analytical data processing means; a second measurement control means for setting measurement conditions, including elements to be measured, according to the group and for giving a second result of measurement by measuring the intensity of the fluorescent X-ray under the measurement conditions thus set; and a quantitative analysis means for determining a quantitatively analyzed value of the sample from the second result of measurement obtained by the second measurement control means with respect to the elements to be measured.

The quantitatively analyzed value referred to above can be applied not only to the content of an element contained in the sample, but also to the amount of deposit of and the film thickness of a thin film where the sample is a thin film formed on a substrate.

According to this feature, by selecting the group to which the sample belongs by means of the qualitative analysis or the semiquantitative analysis, then proper setting measurement conditions such as the measurement time and the wavelength to be measured of a element of interest to be measured and then measuring the intensity of the fluorescent X-ray emitted from the sample under these measurement conditions, a highly accurate qualitative analysis is possible.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Hereinafter, preferred embodiments of the present invention will be described with reference to the accompanying drawings.

Figure 1:
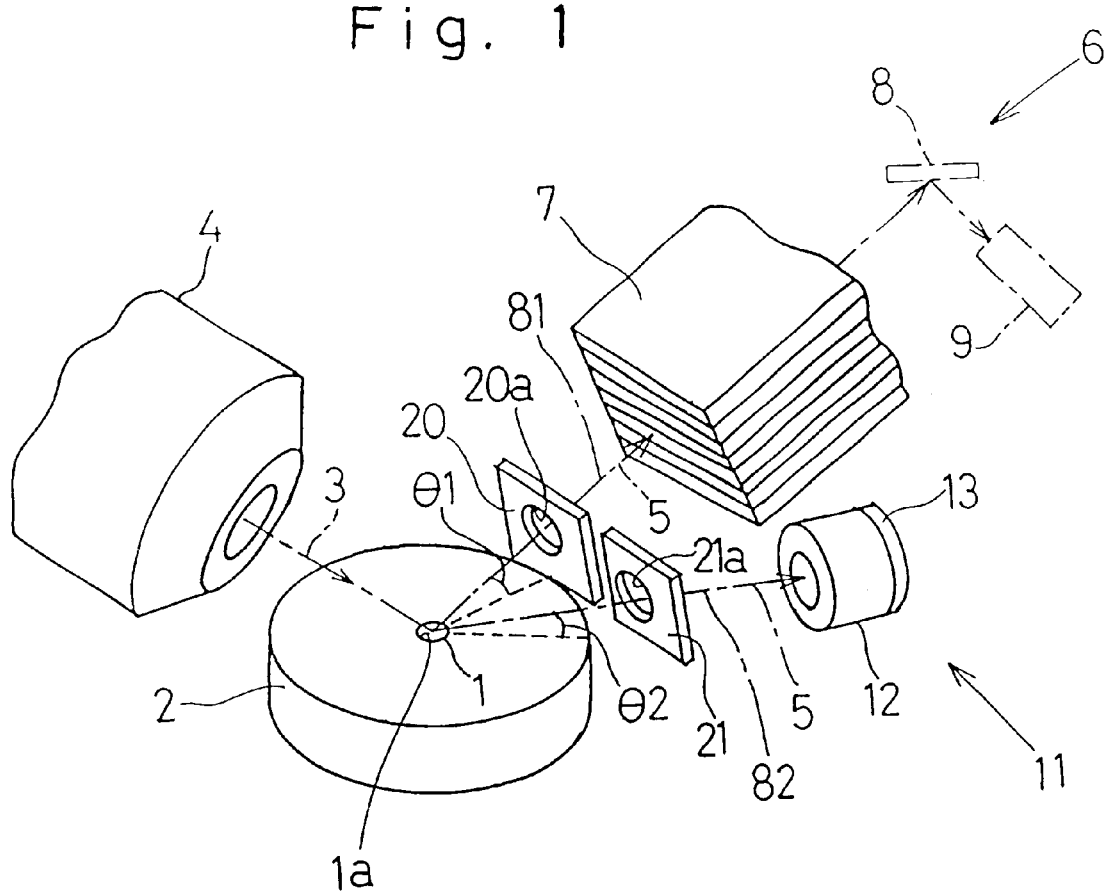
FIG. 1 is a schematic perspective view of a fluorescent X-ray analyzing apparatus according to a first preferred embodiment of the present invention.

A fluorescent X-ray analyzing apparatus according to a first preferred embodiment of the present invention is shown in FIG. 1. The fluorescent X-ray analyzing apparatus shown therein comprises a sample support 2 on which a sample 1 is placed, and an X-ray source 4 for radiating a primary X-ray 3 towards a target area 1a of the sample 1 that is to be measured so as to impinge upon the target area 1a at an angle relative to a surface thereof. The analyzing apparatus also comprises, as a detecting means for detecting a fluorescent X-ray 5 emitted from the target area 1a of the sample 1 as a result of excitation by the primary X-ray 3, a wavelength dispersive type detecting means 6 including a divergent Soller slit 7 for collimating the fluorescent X-rays 5, a spectroscope 8, a first detector 9 and a Goniometer (not shown) for rotating those components in a predetermined positional relation. It is to be noted that the wavelength dispersive type detecting means 6 may not be of a type operable on a parallel method in which parallel beams are drawn through the divergent Soller slit 7 or a light receiving slit (not shown) (which is positioned on a light receiving surface of the first detector 9), but may be of a type operable on a so-called convergent method. In such case, the spectroscope is employed in the form of a curved crystal with a detector positioned at a focal point and no Soller slit for collimating is employed.

The illustrated analyzing apparatus furthermore comprises, as a detecting means, an energy dispersive type detecting means 11 including a second detector of an energy dispersive type in the form of, for example, a semiconductor detector (SSD) 12. The SSD 12 is provided with a cooling means 13 employing a Peltier element. An electroconductive line (not shown) connected with the Peltier element 13 extends externally of an analyzing chamber (not shown), and an electric circuit including an amplifier for supplying an electric current to the Peltier element 13 is disposed outside the analyzing chamber. Since for cooling the SSD a liquid nitrogen is generally used, the analyzing apparatus tends to become bulky because of the provision of a Dewar flask. However, in the present invention, since the Peltier element 13 is employed as the cooling means, the analyzing apparatus can advantageously be assembled in a compact size.

The angle θ1 between the surface of the sample 1 and the first path 81 of travel of the fluorescent X-ray extending between the target area 1a of the sample 1 and the spectroscope 8 and the angle θ2 between the surface of the sample 1 and the second path 82 of travel of the fluorescent X-ray extending between the target area 1a of the sample 1 and the SSD 12 are equal to each other. However, the angles θ1 and θ2 may not be strictly equal to each other and are sufficient if they satisfy the following equation (1).

$$|\sin\theta 1 - \sin\theta 2| < 0.05 \times |\sin\theta 1| \tag{1}$$

Also, the second path 82 of travel of the fluorescent X-ray is shorter than the first path 81 of travel of the fluorescent X-ray. In other words, the SSD 12 is closer to the sample 1 than the spectroscope 8.

The first path 81 of travel of the fluorescent X-ray has a collimator 20 disposed thereon and the second path 82 of travel of the fluorescent X-ray similarly has a collimator 21 disposed thereon. These collimators 20 and 21 has a throttling aperture 20a and 21a of an equal size and are aimed at the same target area 1a from different directions.

The operation of the fluorescent X-ray analyzing apparatus embodying the present invention will now be described.

When the fluorescent X-ray 5 is generated from the sample 1 as a result of radiation of the primary X-ray 3 from the X-ray source 4, the fluorescent X-ray 5 passes through the throttling apertures 20a and 21a. The fluorescent X-ray 5 detected by the energy dispersive type detecting means 11 and the wavelength dispersive type detecting means 6 are processed by a computer (not shown) connected with a pulse height analyzer (not shown).

In the illustrated apparatus, since the angle θ1 of emergence for the wavelength dispersive type is equal to the angle θ2 of emergence for the energy dispersive type, the respective intensities of the fluorescent X-ray measured can be correlated with each other in the form as presented if each of those intensities is multiplied by a predetermined sensitivity coefficient peculiar to the respective detecting system that does not depend on the sample. Accordingly, a processing of a result of analysis performed by the computer can be carried out with no need to take into consideration a complicated correlation of the fluorescent X-ray intensity relative to the angle of emergence. Accordingly, the uncertainty resulting from the complicated correlation of the fluorescent X-ray relative to the angle of emergence can be suppressed, accompanied by increase in analyzing accuracy.

By way of example, the fundamental parameter method is a method in which the stoichiometrically determined intensity of the fluorescent X-ray and the actually measured intensity of the fluorescent X-ray are correlated with each other to determine the content of an element of interest contained in the target area of the sample. With the computer, the result of analysis is processed by correlating the actually measured intensity of the fluorescent X-ray with the stoichiometric intensity thereof which corresponds to the actually measured intensity of the fluorescent X-ray multiplied by a physical constant and a device constant, to thereby determine the content of the element of interest in the target area of the sample. In the illustrated embodiment, since it is sufficient to apply the same correction to the intensities of the fluorescent X-ray measured by the energy dispersive type detecting means 11 and the wavelength dispersive type detecting means 6 respectively and then to correlate them with the stoichiometric intensity, the process performed by the computer can be simplified. Also, since the SSD 12 is positioned closer to the sample 1 than the spectroscope 8, a sufficient sensitivity can be secured in the SSD 12 even though the target area 1a of the sample 1 is very minute, resulting in increase of the analytical accuracy. Accordingly, in the fluorescent X-ray analyzing apparatus capable of being used as both the wavelength dispersive type and the energy dispersive type, a quick and accurate analysis can be achieved.

The sample support 2 is mounted on an XY table for movement in all direction so that the target area 1a can be set at an optimum radiating position. The XY table will be described in detail in connection with a second preferred embodiment of the present invention that follows.

The second embodiment of the present invention will now be described.

Figure 2:
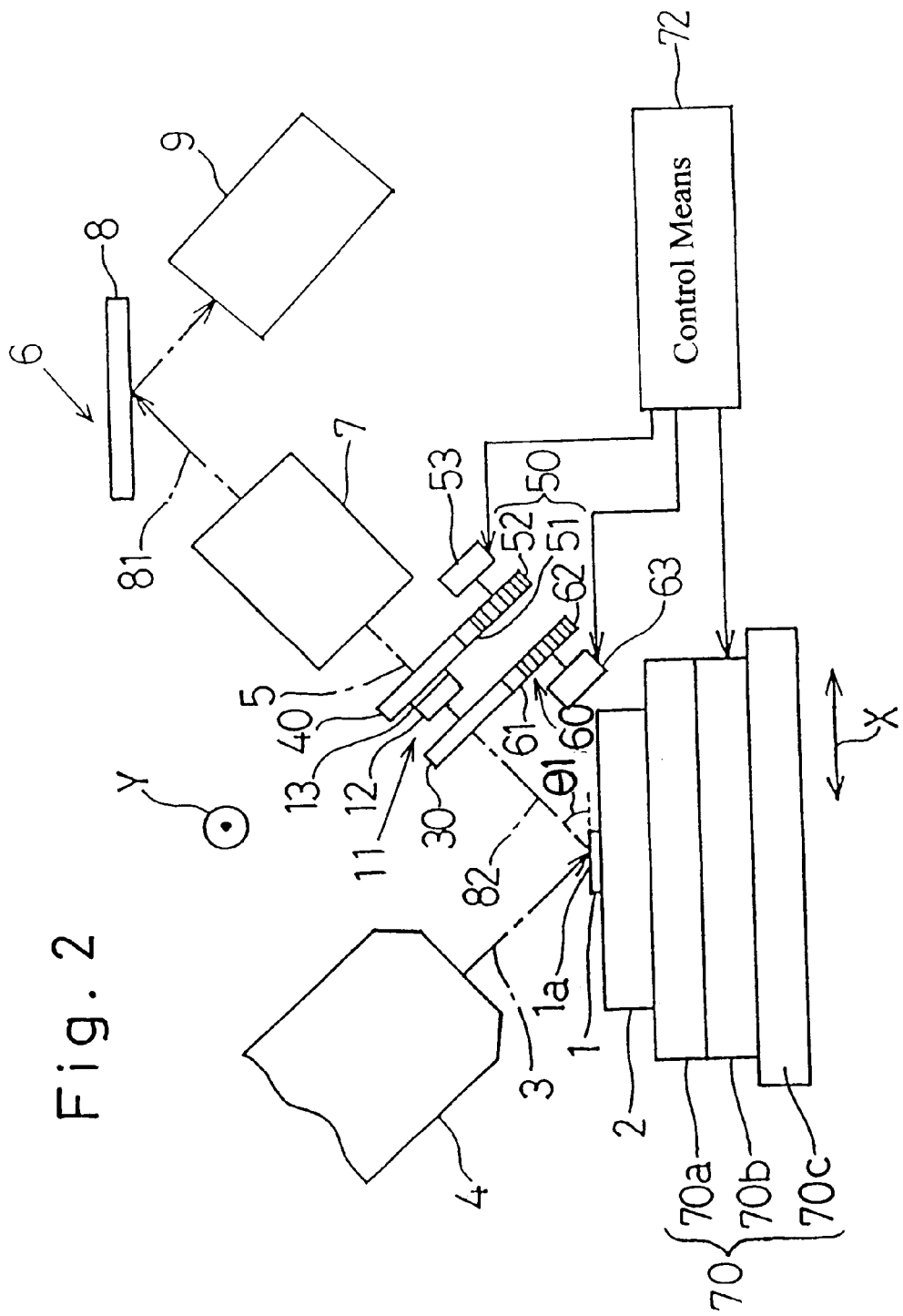
FIG. 2 is a schematic side view of the fluorescent X-ray analyzing apparatus according to a second preferred embodiment of the present invention.
Figure 3:
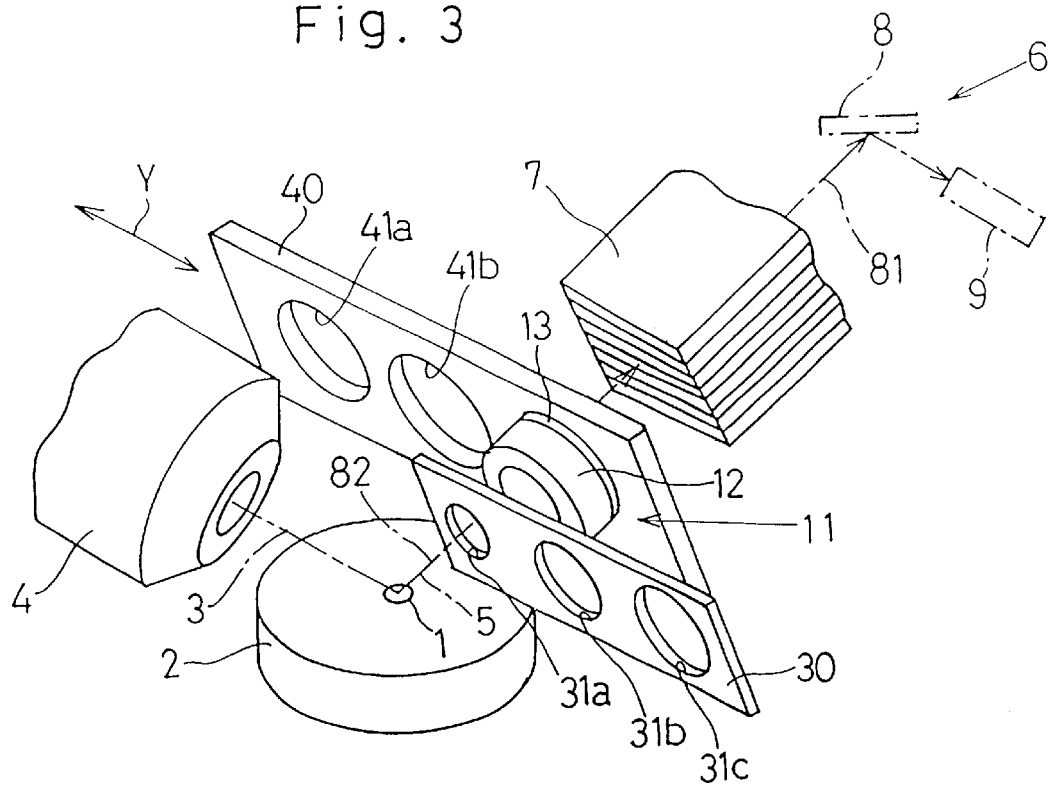
FIG. 3 is a schematic perspective view of the fluorescent X-ray analyzing apparatus of FIG. 2, showing the apparatus set in an energy dispersive type detection mode.

As shown in FIG. 2, as is the case with the analyzing apparatus according to the foregoing embodiment, the analyzing apparatus shown therein comprises a sample support 2 on which a sample 1 is placed, an X-ray source 4, and a wavelength dispersive type detecting means 6 including a divergent Soller slit 7, a spectroscope 8 and a first detector 9. A plate-shaped first collimator 30 is disposed on the path 81 of travel of the fluorescent X-ray between the sample 1 and the detecting means 6. As shown in FIG. 3, the first collimator 30 has a plurality of, for example, three throttling apertures 31a, 31b and 31c of different diameters defined therein in a row. The first collimator 30 may not be always limited to that of a plate-like shape, but may be of any suitable shape, for example, having an upper wall or a stepped wall adjacent the sample for improving the S/N ratio of the fluorescent X-ray generated from the sample, such as disclosed in the Japanese Patent Application No. 10-310056, the disclosure of which is herein incorporated by reference. Also, a plate-shaped second collimator 40 having a plurality of, for example, two throttling apertures 41a and 41b defined therein is interposed between the first collimator 30 and the spectroscope 8.

The illustrated analyzing apparatus also comprises, as a detecting means, an energy dispersive type detecting means 11 including an SSD 12 that is a second detector of an energy dispersive type. The SSD 12 is carried by the second collimator 12 at a location laterally of and on one side of the throttling aperture 41b remote from the throttling aperture 41a. This SSD 12 is capable of detecting the fluorescent X-ray 5 that has passed through one of the throttling apertures 31a, 31b and 31c in the first collimator 30. As is the case with the foregoing embodiment, the SSD 12 is provided with a cooling means 13 of a kind utilizing the Peltier element. It is to be noted that the second collimator 40 having the throttling apertures 41a and 41b defined therein may be dispensed with and, in such case, only the SSD 12 has to be supported at a location behind the first collimator 30 for movement into and out of the first path 81 of travel of the fluorescent X-ray.

As shown in FIG. 2, the SSD 12 is drivingly coupled with a detector driving mechanism 50 for enabling the SSD 12 to be moved between an operative position, in which the SSD 12 is brought into alignment with the first path 81 of travel of the fluorescent X-ray, and a retracted position in which the SSD 12 is clear from the first path 81 of travel of the fluorescent X-ray. This detector driving mechanism 50 includes a rack 51 fitted to a lower portion of the second collimator 40 and a pinion 52 coupled with a pulse-responsive stepper motor 53. The second collimator 40 is mounted movably on a guide member (now shown) and, since the rack 51 is engaged with the pinion 52, drive of the stepper motor 53 results in a sliding motion of the second collimator 40 in a direction shown by Y along the guide member. When the second collimator 40 is driven to the operative position and is therefore aligned with the first path 81 of travel of the fluorescent X-ray, the first path 81 of travel of the fluorescent X-ray from the target area 1a of the sample 1 towards the spectroscope 8 and the second path 82 of travel of the fluorescent X-ray from the target area 1a of the sample 1 towards the SSD 12, which is an energy dispersive type detector, lie on the same axis.

The first collimator 30 is also mounted movably on a guide member (not shown) that extends in the direction Y which is perpendicular to the sheet of the drawing of FIG. 2. A rack 61 is secured to a lower portion of the first collimator 30 and is drivingly meshed with a pinion 62 coupled with a pulse-responsive stepper motor 63. Accordingly, in a manner similar to the second collimator 40, the first collimator 30 can be slid in the direction Y along the guide member (not shown) by the drive of the stepper motor 63. Thus, the rack 51 and the pinion 62 coupled with the stepper motor 63 constitute a driving mechanism 60 for the first collimator 30.

The analyzing apparatus shown in FIG. 2 furthermore comprises a sample driving mechanism 70 such as, for example, an XY stage for moving the target area 1a of the sample 1 placed on the sample support 2. The sample driving mechanism 70 includes top, intermediate and bottom benches 70a, 70b and 70c stacked one above the other for movement in different directions. More specifically, the top bench 70a on which the sample support 2 is fixedly mounted is movable in a left and right direction X perpendicular to the direction Y relative to the intermediate bench 70b while the intermediate bench 70b is movable in the direction Y relative to the bottom bench 70c positioned below the intermediate bench 70b. The directions X and Y lie in the orthogonal coordinates defined in a virtual radiating plane. Instead of the use of the XY stage for the sample driving mechanism 70, an rθ stage may be employed therefore, in which case rθ represents a polar coordinate defined on the virtual radiating plane with a pole occupied by a center of the surface of the sample. In other words, the sample driving mechanism 70 moves or rotate the sample 1 to move a portion of the sample 1, which will be the target area 1a, relative to the X-ray source 4 and the wavelength dispersive type detecting means 6 or the X-ray source 4 and the energy dispersive type detecting means 11 so that the sample surface can follow the virtual radiating plate.

The second collimator 40, the first collimator 30 and the XY stage 70 are controlled by a control means 72. Depending on whether the fluorescent X-ray is to be detected by the energy dispersive type detecting means 11 or whether the fluorescent X-ray is to be detected by the wavelength dispersive type detecting means 6, the control means 72 controls the second collimator 40. In other words, where the fluorescent X-ray is to be detected by the energy dispersive type detecting means 11, the SSD 12 fitted to the second collimator 40 is brought to the operative position in alignment with the first path 81 of travel of the fluorescent X-ray. On the other hand where the fluorescent X-ray is to be detected by the wavelength dispersive type detecting means 6, the second collimator 40 is brought to the retracted position out of alignment with the first path 81 of travel of the fluorescent X-ray.

The control means 72 also controls respective positions of the first and second collimators 30 and 40 in such a way as to select the throttling aperture in the collimator, depending on the size of the target area 1a of the sample 1, so that only the fluorescent X-ray 5 generated from the target area 1c can be received by the detecting means 6. More specifically, the control means 72 controls one or both of stepper motors 53 and 63 for driving the first collimator 30 and the second collimator 40, respectively, so that where the energy dispersive type detecting means 11 is utilized for the detection of the fluorescent X-ray, one of the throttling apertures 31a, 31b and 31c in the first collimator 30 is selected, but where the wavelength dispersive type detecting means 6 is used for the detection of the fluorescent X-ray, one of the throttling apertures 31a, 31b and 31c in the first collimator 30 or of the throttling apertures 41a and 41b in the second collimator 40 is selected.

The control of the XY stage 70 by the control means 72 is to move the sample support 2 to thereby move the target area 1a of the sample 1.

The analyzing apparatus according to the second embodiment of the present invention operates in the following manner.

It is assumed that the target area 1a of the sample 1 is very minute in size and a fluorescent X-ray emitted from an unknown element contained in the sample 1, particularly in the target area 1a is desired to be analyzed. Specifically, after the target area 1a has been qualitatively analyzed, the quantitative analysis is carried out.

At the outset, as shown in FIG. 2, the sample 1 is placed on the sample support 2 in alignment with a center point thereof. After the target area 1 in the sample 1 has been determined, a parameter descriptive of a result of such determination is inputted in the control means 72. Parameters descriptive of an analysis desiring to perform the qualitative analysis, that is, an energy dispersive type detection and of the size of the target area 1a are also inputted to the control means 72.

Once these parameters have been inputted to the control means 72, the control means 72 controls the XY stage 70 to move the sample support 2 to a position where the target area 1a of the sample 1 is brought to a radiating position receiving the primary X-ray 3. The control means 72 also controls the stepper motor 53 to advance the second collimator 40 with the SSD 12 consequently brought to the operative position in alignment with the first path 81 of travel of the fluorescent X-ray. As the stepper motor 53 is so driven, the second collimator 40 is moved in the direction Y to enter the first path 81 of travel of the fluorescent X-ray between the sample 1 and the wavelength dispersive type detecting means 6. The control means 72 furthermore controls the stepper motor 63 so that one 31a of the throttling apertures (FIG. 3) of the first collimator 30 which is appropriate to the inputted size of the target area 1a can be selected, that is, only the fluorescent X-ray 5 emitted from the target area 1a of the sample 1 can enter the SSD 12. As this stepper motor 63 is so driven, the throttling aperture 31a of the first collimator 30 is brought into alignment with the first path 81 of travel of the fluorescent X-ray between the sample 1 and the wavelength dispersive type detecting means 6.

As shown in FIG. 3, when during the condition shown in FIG. 3 the fluorescent X-ray 5 is generated from the sample 1 as a result of radiation of the primary X-ray 3 from the X-ray source 4, the fluorescent X-ray 5 pass through the throttling aperture 31a of the first collimator 30 and is then detected by the SSD 12. The intensity of the fluorescent X-ray detected by the SSD 12 is processed by a computer (not shown) to give a wavelength distribution characteristic in a short length of time to thereby enable the qualitative analysis thereof Although the target area 1 is a very minute site, the SSD 12 is positioned closer to the sample than the spectroscope 8 and, therefore, a sufficient sensitivity can be secured in the SSD 12, resulting in analytical accuracy.

Figure 4:
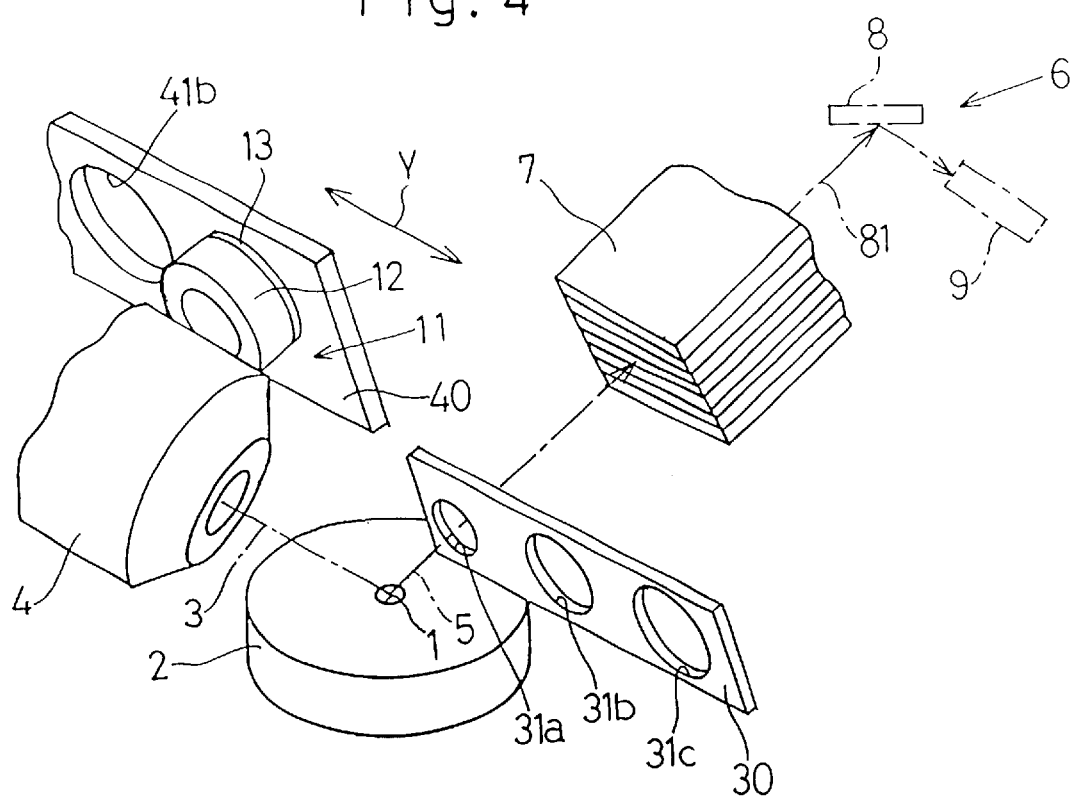
FIG. 4 is a schematic perspective view of the fluorescent X-ray analyzing apparatus of FIG. 2, showing the apparatus set in a wavelength dispersive type detection mode.

After the wavelength distribution characteristic has been examined in this way, the second collimator 40 is retracted out of the first path 81 of travel of the fluorescent X-ray as shown in FIG. 4. Thereafter, based on this wavelength distribution characteristic the wavelength to be measured is determined and, in order to analyze and detect the fluorescent X-ray corresponding to the determined wavelength, the Goniometer (not shown) adjusts the respective position of the spectroscope 8 and the first detector 9. In this condition, the fluorescent X-ray 5 generated from the sample 1 passes through the throttling aperture 31a of the first collimator 30, collimated by the divergent Soller slit 7, analyzed by the spectroscope 8 and finally detected by the first detector 8. The intensity of the fluorescent X-ray so detected is processed by the computer (not shown) to accomplish an analysis a desired range of wavelengths to be examined in detail, that is, to accomplish the quantitative analysis.

As hereinabove described, the qualitative analysis is carried out by the utilization of the energy dispersive type detecting means 11, followed by the quantitative analysis of the particular element of interest by the utilization of the wavelength dispersive type detecting means 6 and, accordingly, a quick and accurate analysis of the fluorescent X-ray can be performed.

As discussed above the first path 81 of travel of the fluorescent X-ray and the second path 82 of travel of the fluorescent X-ray lie on the same axis. Accordingly, even though the sample 1 has a rough surface full of minute surface irregularities, the SSD 12 that is the second detector of the energy dispersive type detecting means 11 and the spectroscope 8 of the wavelength dispersive type detecting means 6 are aligned with the target area 1a of the sample 1 from the same direction and, therefore, no deviation occur in respective results of measurement. Thus, the respective results of measurement can be correlated with each other in the form as presented after they have been multiplied by a predetermined sensitive coefficient that does not depend on the type of the sample and that is peculiar to the respective detection system. This makes it possible to increase the analytical accuracy. Moreover, since the throttling aperture 31a of the first collimator 30 is concurrently employed for the energy dispersive detecting means 11 and the wavelength dispersive type detecting means 6, the quantitative analysis can be carried out by the wavelength dispersive type detecting means based on the qualitative analysis performed by the energy dispersive type detecting means 11 as hereinbefore described.

Also, in the practice of the second embodiment of the present invention, where the fluorescent X-ray generated from the target area 1a of the sample 1 which is large in size is desired to be detected and analyzed by the wavelength dispersive type detecting means 8, the first collimator 30 is retracted out of the first path 81 of travel of the fluorescent X-ray while either the throttling aperture 41a or the throttling aperture 41b of the second collimator 40 is brought into alignment with the first path 81 of travel of the fluorescent X-ray. This can be accomplished as the control means 72 controls the driving mechanism 50 in a manner similar to advance of the SSD 12 into the first path 81 of travel of the fluorescent X-ray and, therefore, switching between the throttling apertures 41a and 41b can easily be accomplished.

A third preferred embodiment of the present invention will now be described.

Figure 5:
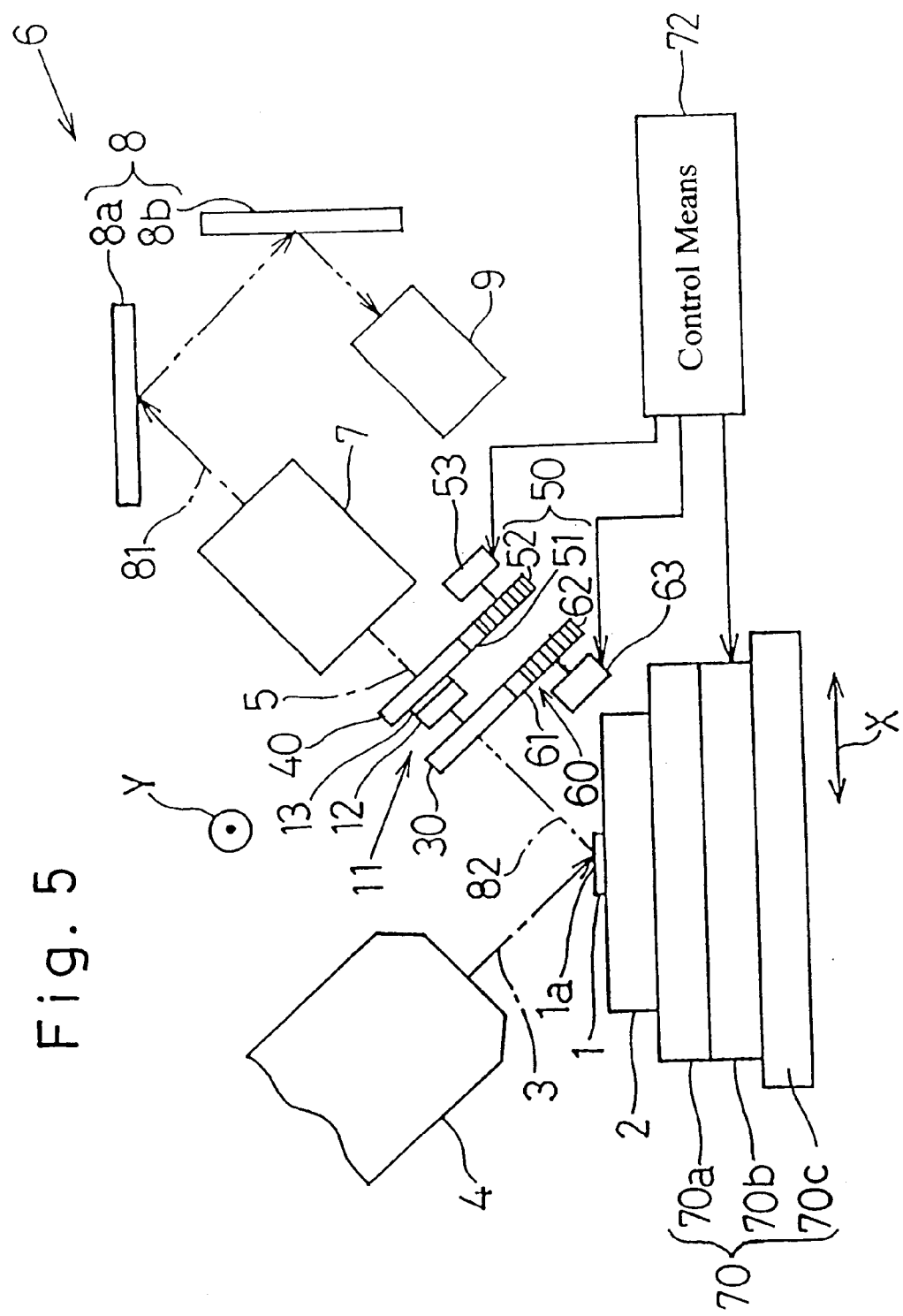
FIG. 5 is a schematic side view of the fluorescent X-ray analyzing apparatus according to a third preferred embodiment of the present invention.

The analyzing apparatus according to the third embodiment of the present invention differs from that according to the second embodiment in that as shown in FIG. 5, the wavelength dispersive type detecting means 6 although comprised of a single crystal spectroscope in the second embodiment is employed in the form of a double crystal spectroscope 8 including a first spectroscopic crystal element 8a and a second spectroscopic crystal element 8b positioned fore and after along the first path 81 of travel of the florescent X-ray so as to direct the first fluorescent X-ray from the Soller slit 7 towards the first detector 9. The double crystal spectroscope 8 is of a structure in which the fluorescent X-ray spectroscopically analyzed by the first spectroscopic crystal element 8a can be again spectroscopically analyzed by the second spectroscopic crystal element 8b. Accordingly, the double crystal spectroscope 8 has a very high wavelength resolving power and is capable of detecting even slight change in fluorescent X-ray wavelength brought about by a chemical condition, wherefore the analyzing apparatus itself can be utilized for analysis of the chemical condition. The analyzing apparatus according to the third embodiment of the present invention is therefore utilizable for the qualitative analysis by means of the energy dispersive type detecting means 11 and also for analysis of the chemical condition by means of the wavelength dispersive detecting means 6 including the double crystal spectroscope 8. In such case, as compared with the qualitative analysis with the use of the wavelength dispersive detecting means including the one crystal spectroscope such as in the foregoing embodiment, no replacement of component parts is required, conveniently accompanied by reduction in length of time required to switch from the qualitative analysis over to the analysis of the chemical condition. Also, while with the double crystal spectroscope the range of wavelengths that can be measured has been limited because of a mechanical limitation restricting the range of rotation of the crystal at the later stage, the combined use of it with the energy dispersive type detecting means 11 makes it possible to accomplish the analysis a wavelength region of coexistent elements even where only the chemical condition of a particular element is desired to be analyzed, and therefore, a sufficient qualitative analysis is possible in that information on the composition of the coexistent elements can be obtained.

Figure 6:
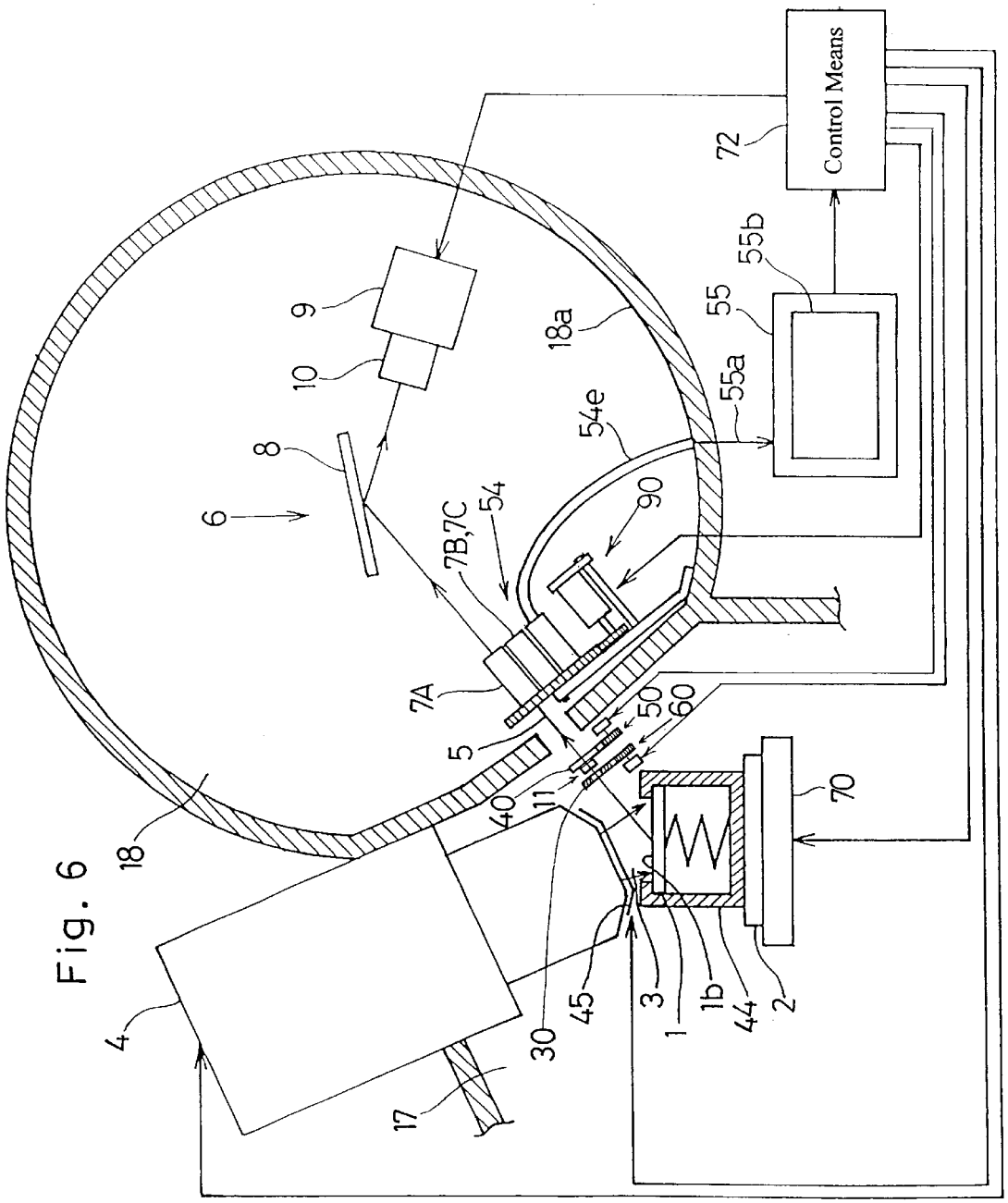
FIG. 6 is a schematic side view of the fluorescent X-ray analyzing apparatus according to a fourth preferred embodiment of the present invention.
Figure 7:
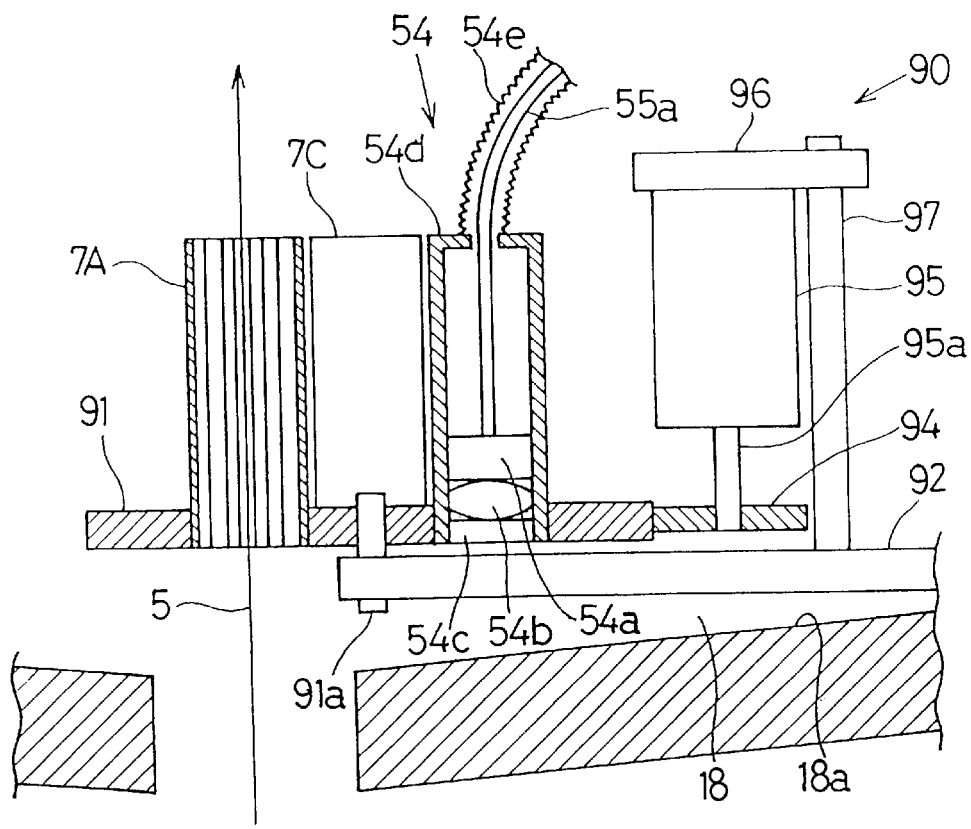
FIG. 7 is a schematic sectional view showing a selecting means and an imaging means both employed in the fluorescent X-ray analyzing apparatus shown in FIG. 6.
Figure 8:
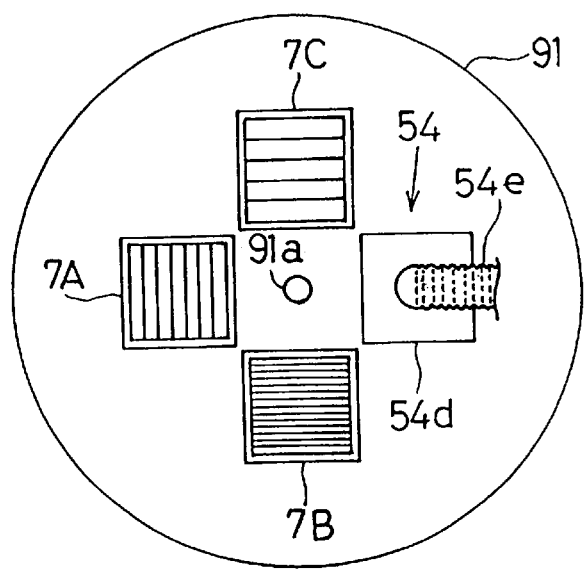
FIG. 8 is a plan view of the selecting means and the imaging means shown in FIG. 7.

Referring now to FIGS. 6 to 8, the analyzing apparatus according to a fourth preferred embodiment of the present invention will be described.

As best shown in FIG. 6, the analyzing apparatus differs from any of the previously described embodiments of the present invention in that the first and second collimators 30 and 40 are accommodated within a sample chamber 17 within which the sample 1 is radiated by the primary X-ray 3 and in that the first collimator 30 is disposed at a location generally intermediate between the SSD 12, forming the second detector of the energy dispersive type detecting means 11, and the sample 1 placed on the sample support 2.

The wavelength dispersive type detecting means 6 employed in the analyzing apparatus shown in FIG. 6 includes a light receiving Soller slit 10 allowing passage therethrough of the fluorescent X-ray 5 that has been spectroscopically analyzed by the spectroscope 8. As is the case with the analyzing apparatus according to the second embodiment of the present invention, the analyzing apparatus shown therein includes a sample drive mechanism 70 for moving the target area 1a of the sample placed on the sample support 2. It is to be noted that the sample 1 is accommodated in a sample holder 44 and that although the sample drive mechanism 70 is shown as employed in the form of a so-called rθ stage, an XY stage may be employed therefore. In either case, the direction of movement of the sample holder 44 accommodating therein the sample 1 has to be carefully determined so that the movement of the sample holder 44 caused by the sample drive mechanism will not be hampered by obstructions.

A filter plate 45 is preferably disposed in front of the X-ray source 4 so that the primary X-ray 3 appropriate to the sample 1 will radiate the sample 1. The filter plate 45 includes a plurality of filters having a different light transmission characteristic and a light shield for shielding passage of the X-ray emitted from the X-ray source 4 in a direction perpendicular to the sheet of the drawing of FIG. 6, This filter plate 45 is capable of being moved by a motor and a drive mechanism, both not shown, in a direction perpendicular to the sheet of the drawing of FIG. 6. It is to be noted that the filter plate 45 may be of a generally disc shape including the plural filters and the light shield arranged in a circumferential direction thereof and may be rotated by the control means 72.

The illustrated analyzing apparatus also includes an imaging means 54 for imaging a surface 1b of the sample 1 placed on the sample support 2 through the sample holder 44 to form an image of the sample surface 1b, a display means 55 such as, for example, a liquid crystal panel for displaying the image of the sample surface 1b formed by the imaging means 54, and a control means 72 for controlling the rθ stage 70 so that the fluorescent X-ray 5 emitted from a site of the sample 1 (which site is to be understood as including the sample in its entirety where the sample is very minute in size) that is specified based on the image of the sample surface 1b displayed by the display means 55 can be sensed by the energy dispersive type detecting means 11 or the wavelength dispersive type detecting means 6. The imaging means 54 is disposed within a spectral analyzing chamber 18 in which the fluorescent X-ray 5 from the sample is analyzed.

As shown in detail in FIG. 7, the imaging means 54 comprises a tubular casing 54d, a windowpane 54c such as, for example, a lead glass plate fitted to a front end of the tubular casing 54d, an objective lens 54b positioned behind the windowpane 54c within the tubular casing 54d for passage therethrough of light incident through the windowpane 54c, a charge-coupled device (CCD) 54a housed within the tubular casing 54d for capturing an imagewise light having passed through the lens 54b, and a flexible tube 54e having one end connected with a rear end of the tubular casing 54d remote from the windowpane 54c and the opposite end connected with an inner wall 18a of the spectral analyzing chamber 18 as shown in FIG. 6. A cable 55a drawn from the CCD 54a extends within the flexible tube 54e and then through the wall of the spectral analyzing chamber 18 to the display means 55 for transmitting an image signal indicative of the image of the sample surface 1b from the CCD 54a to the display means 55 to allow the latter to display the image of the sample surface 1b.

It is to be noted that a reflector as a part of the imaging means 54 may be disposed within the spectral analyzing chamber 18 so that an mirror image formed on the reflector can be imaged by the CCD 54a, positioned externally of the spectral analyzing chamber 18, through a window formed in the wall defining the spectral analyzing chamber 18. It is also to be noted that an optical fiber cable may be employed as a part of the imaging means 54, having one end positioned within the spectral analyzing chamber 18 and the opposite end extending through the wall of the spectral analyzing chamber 18 and connected with the CCD 54a positioned externally of the spectral analyzing chamber 18. In this alternative arrangements, a portion of the wall of the spectral analyzing chamber 18 where the window is defined or where the optical fiber cable extends has to be sealed. Preferably, a lighting element (not shown) for illuminating the sample surface 1b during imaging is preferably positioned in the vicinity of a front portion of the imaging means 54 or in the vicinity of the windowpane 54c as viewed in FIG. 7.

The analyzing apparatus shown therein includes, as shown in FIG. 6, a divergent Soller slit 7 and an imaging means 54 both positioned between the second collimator 40 and the spectroscope 8, and a selector means 90 for selectively positioning one of the divergent Soller slit 7 and the imaging means 54 in position to align with the sample 1 placed on the sample support 2. Specifically referring to FIG. 8 which represents a plan view of a portion of FIG. 7, in this analyzing apparatus, three divergent Soller slits 17A, 17B and 17C having a different resolving power and a casing 54d including the CCD 54a of the imaging means 54 are mounted on a single driven gear wheel 91 mounted on a shaft 91a. The divergent Soller slits 7A to 7C and the casing 54d are arranged on the driven gear wheel 91 with their respective longitudinal axes lying parallel to and spaced an equal distance from the shaft 91a and spaced 90° circumferentially from each other about the shaft 91a. The selector 90 inclusive of the driven gear wheel 91 is so structured and so configured as will now be described with particular reference to FIG. 7.

Referring to FIG. 7, the shaft 91a of the driven gear wheel 91 is rotatably supported by a base 92 fixed to the inner wall of the spectral analyzing chamber 18 with the driven gear wheel 91 meshed with a drive gear 94. The drive gear 94 is in turn mounted on a drive shaft 95a of a drive motor 95 for rotation together therewith. The drive shaft 95a of the drive motor 95 extends parallel to the shaft 91a of the driven gear wheel 91 while the drive motor 95 is fixedly supported by the base 92 through a support plate 96 and an arm 97 lying generally perpendicular to the support plate 96. With the selector means 90 so structured and so configured as described above, one of the divergent Soller slits 7A to 7C and the imaging means 54 can be selectively brought in position to align with the sample 1. With the analyzing apparatus according to this embodiment now under discussion, the selector means 90 for driving the imaging means 54 concurrently serves as a selector for the divergent Soller slits 7A to 7C and, therefore, the analyzing apparatus can be simplified in structure.

Figure 13:
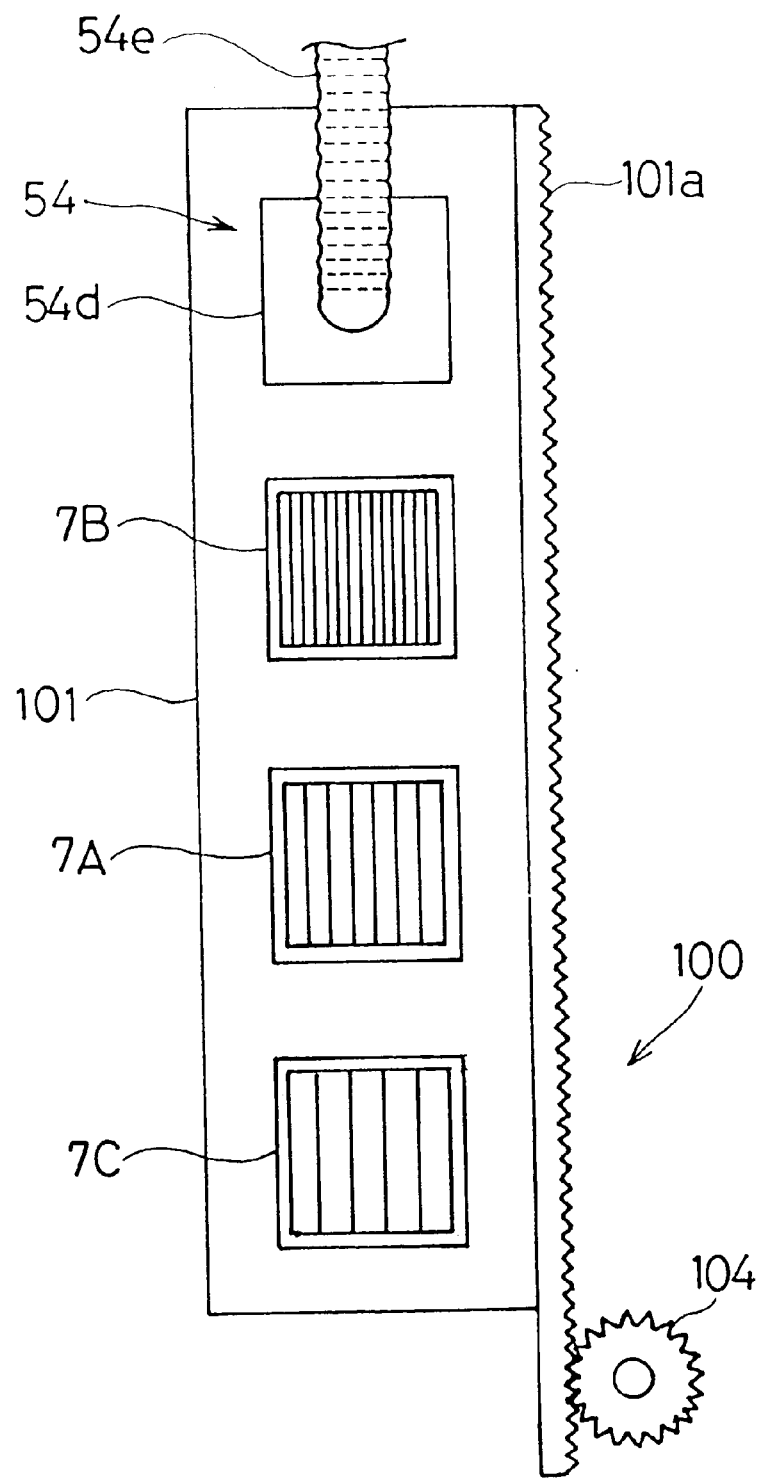
FIG. 13 is a plan view showing a modified selecting means employed in the fluorescent X-ray analyzing apparatus according to the fourth embodiment of the present invention.

Although in the embodiment shown in FIGS. 6 to 8 each of the drive gear 94 and the driven gear wheel 91 forming respective parts of the selector means 90 has been shown and described as employed in the form of a spur gear, a pinion 104 and a rack 101a may be employed instead of the drive gear 94 and the driven gear wheel 91, respectively, to complete an alternative selector means 100 as shown in FIG. 13. Referring to FIG. 13, the divergent Soller slit 7 and at least a portion of the imaging means 54 are mounted in side-by-side relation to each other on a carrier plate 101 so as to extend in a vertical direction as viewed in FIG. 13. The carrier plate 101 has the rack 101a fixed thereto and is adapted to be driven by the pinion 104 meshed with the rack 101a, in a vertical direction as viewed therein. Other structural features than the selector means 100 are identical with those in the analyzing apparatus according to the second embodiment of the present invention.

The operation of the analyzing apparatus shown in FIGS. 6 to 8 will now be described.

Referring to FIG. 6, at the outset, after the sample holder 44 containing the sample 1 is placed on the sample support 2 and a parameter descriptive of the start of setting of a minute target area of the sample 1 is inputted in the control means 72, the control means 72 causes the drive mechanisms 50 and 60 to retract the first and second collimators 30 and 40 in a direction perpendicular to the sheet of the drawing of FIG. 6 so that the first and second collimators 40 and 50 will not constitute an obstruction to the imaging, and also cause the selector means 90 to bring the imaging means 54 in position to align with the sample 1 so that the image of the sample surface 1b can be imaged and subsequently displayed by the display means 55. At this time, the filter plate 45 is moved to a position where the light shield opaque to the X-ray from the X-ray source 4 is brought in front of the X-ray source 4. This movement is necessitated to eliminate any possible problem such as discoloration of the lens 54b (FIG. 7) of the imaging means 54 which would otherwise occur when the lens 54b is exposed to the X-ray from the X-ray source 4 for an extended length of time. At the same time, although the sample surface 1b is illuminated by the lighting element of the imaging means 54, illuminating light from the lighting element is reflected from a rear surface (undersurface) of the filter plate 45 to further illuminate the sample surface 1b.

The display means 55 employed in the practice of the illustrated embodiment of the present invention is of a kind having a touch panel on a screen 55b thereof and can therefore concurrently serve as an input means. Accordingly, an operator can specify and input the minute target area by applying a pen tip directly to an arbitrarily chosen position of the image of the sample surface 1b displayed on the screen 55b.

Alternatively, a cursor appearing on the screen 55b of the display means 55 may be moved by means of an input means (not shown) to an arbitrarily chosen position of the image of the sample surface 1b displayed on the screen 55b to specify and input the target area to be measured.

When an end command indicative of termination of specifying of the target area is inputted, the control means 72 calculates an appropriate angle of rotation and/or an appropriate distance of linear movement of the sample 1, that are effected by the rθ stage 70, with the arbitrarily chosen position of the image, so that the rθ stage 70 can be controlled to set the minute target area in position to allow the specified minute target area of the sample 1 to be most radiated by the primary X-ray 3 to emit the fluorescent X-ray and also to allow the emitted fluorescent X-ray to be incident upon the energy dispersive type detecting means 11. Thus, with the analyzing apparatus according to the fourth embodiment of the present invention, since the minute target area can be specified by looking at the image of the sample surface 1b on the sample support 2 that is directly videoed immediately before the measurement, the minute target area of the sample 1 can be quickly and accurately determined.

The control means 72 does not only performs the setting of such a minute target area in the manner described hereinabove, but also moves the first and second collimators 30 and 40 in the direction perpendicular to the sheet of the drawing to properly position the throttling aperture 31 (FIG. 3) and the energy dispersive type detecting means 11. The operator of the analyzing apparatus selects one of the filters in the filter plate 45 according to the wavelength of the fluorescent X-ray to be generated. This selection may be carried out by the control means 72 by inputting the wavelength or the like of the fluorescent X-ray 5 to be generated. Once the proper filter has been selected, the control means 72 causes the X-ray source 4 to apply the primary X-ray 3 to the sample 1, the intensity of which is subsequently measured by the energy dispersive type detecting means 11 including the SSD 12. Thus, with the analyzing apparatus according to the fourth embodiment of the present invention, the wavelength distribution characteristic of the fluorescent X-ray 5 of a relatively low intensity emitted from the target area can be examined broadly in a short length of time by means of the energy dispersive detecting means 11 having a relatively high sensitivity.

Then, the operator has to input to the control means 72 a wavelength range to be analyzed in detail, after the broad wavelength distribution characteristic has been examined. In response thereto, the first and second collimators 30 and 40 are moved in a direction perpendicular to the sheet of the drawing to properly position the throttling aperture (FIG. 3) and to retract the second collimator 40 together with the energy dispersive type detecting means 11. The operator also causes the selector means 90 to bring one of the divergent slits, for example, the divergent slit 7A, appropriate to the wavelength of the fluorescent X-ray 5 to be analyzed to a position aligned with the sample 1. This selection may be carried out by the control means 72. Similarly, one of the filters in the filter plate 45 is also selected. Once the proper divergent slit 7A and the proper filter have been selected, the control means 72 causes the X-ray source 4 to apply the primary X-ray 3 to the sample 1 and then causes the wavelength dispersive type detecting means 6 to measure the intensity of the fluorescent X-ray 5 generated over a wavelength range desired to be analyzed in detail. It is to be noted that where a plurality of minute target areas to be analyzed are specified all at a time, the setting and measurement of the plural target areas are carried out in the order, for example, as specified.

As described above, with the analyzing apparatus according to the fourth embodiment of the present invention, the wavelength distribution characteristic of the fluorescent X-ray 5 of a relatively low intensity from the minute target area of the sample is roughly examined in a short length of time by means of the energy dispersive type detecting means 11, followed by measurement of the intensity of the fluorescent X-ray 5 over the necessary or desired range of wavelengths by means of the wavelength dispersive type detecting means 6 having a high resolving power. Accordingly, a quick and accurate analysis is possible with respect to the minute target area of the sample once chosen. In other words, the arbitrarily chosen minute target area of the sample 1 can be quickly and accurately determined and the analysis of the minute target area so determined can be performed quickly and accurately. Therefore, a quick and accurate analysis of the arbitrarily chosen minute target area of the sample 1 can be performed.

Figure 9:
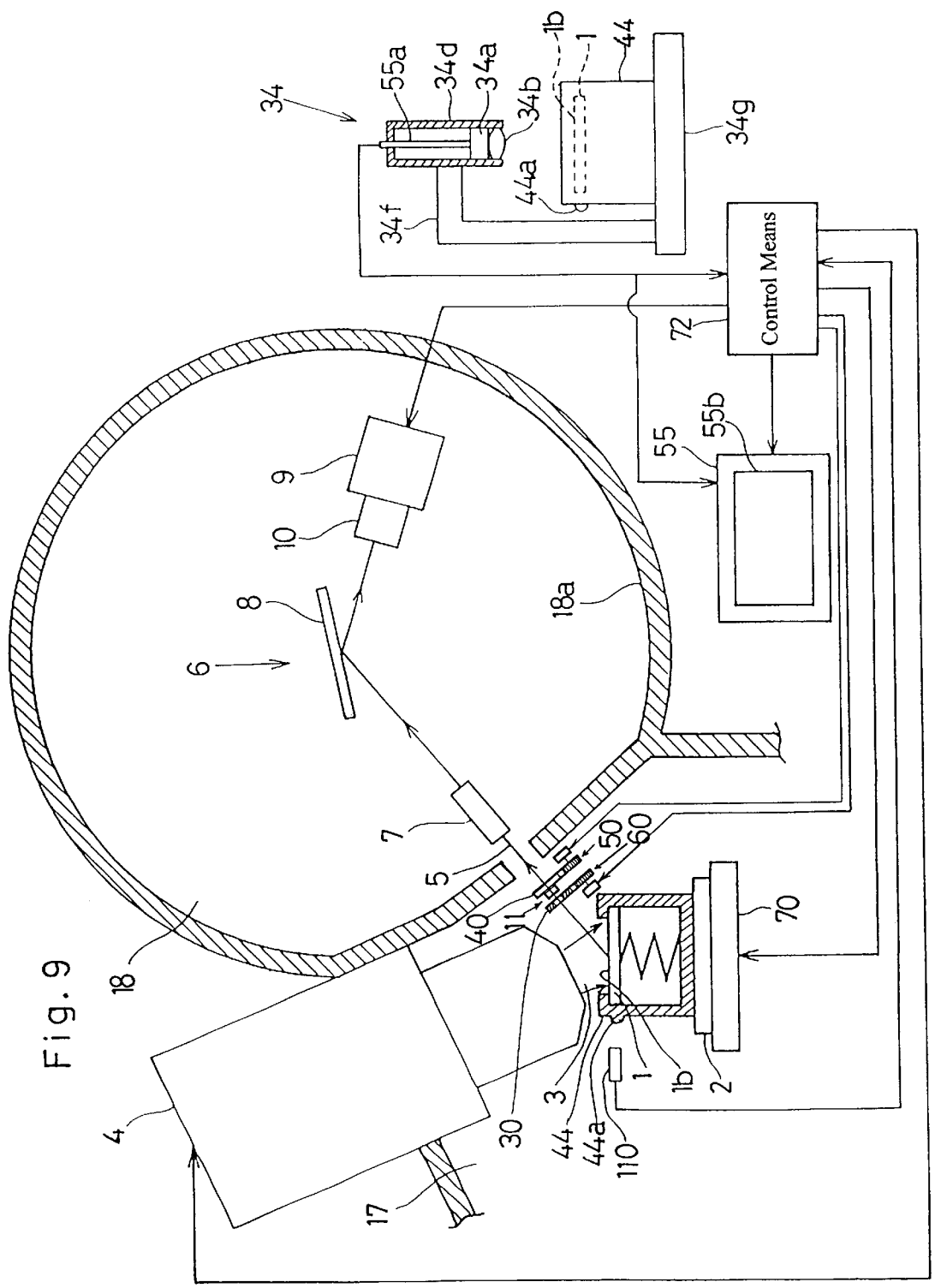
FIG. 9 is a schematic side view of the fluorescent X-ray analyzing apparatus according to the fifth preferred embodiment of the present invention.

FIG. 9 illustrates the analyzing apparatus according to a fifth preferred embodiment of the present invention.

Referring now to FIG. 9, the analyzing apparatus shown therein differs from the analyzing apparatus according to the fourth embodiment in that the imaging means 34 is positioned externally of the sample chamber 17 and also of the spectral analyzing chamber 18, in that the surface 1b of the sample 1 before placement on the sample support 2 is imaged and in that neither the selector means 90 nor the filter plate 45 such as employed in the analyzing apparatus according to the fourth embodiment is employed. Other structural features than those mentioned above are similar to those in the analyzing apparatus according to the previously described embodiment and, are not therefore described for the sake of brevity.

The imaging means 34 employed in the analyzing apparatus according to the fifth embodiment is in its entirety positioned in the atmospheric pressure and comprises a tubular casing 34d, an objective lens 34b fitted to a front end of the tubular casing 34d, a charge-coupled device (CCD) 34a housed within the tubular casing 34d for capturing an imagewise light having passed through the lens 34b, a holder bench 34g on which the sample holder 44 containing the sample 1 is placed, and a support fixture 34f for supporting the tubular casing 34d above the holder bench 34g with the CCD 34a aimed at the sample surface 1b. The cable 55a connected to the display means 55 extends outwardly from a rear end of the tubular casing 34d of the imaging means 34 to transmit the imagewise signal generated by the CCD 34a to the display means 55.

The analyzing apparatus according to the fifth embodiment of the present invention operates in the following manner.

At the outset, the sample holder 44 containing the sample 1 is placed on the holder bench 34g immediately below the CCD 34a so as to be directed in a predetermined direction. To facilitate the alignment of the sample holder 44 with the CCD 34a, the sample holder 44 may have a projection 44a that is utilized to align with a marking formed on the holder bench 34a when the sample holder 44 is placed on the holder bench 34g. After the placement of the sample holder 44 on the holder bench 34g, and when a command indicating that the image of the sample surface 1b is to be stored is inputted to the control means 72, the imaging means 34 scans the sample surface 1b to form an image of the sample surface 1b, which is subsequently stored. When at the time measurement conditions are specified and inputted, a start command instructing the control means 72 to start the setting of a target area to be measured is inputted, the control means 72 causes the stored image of the sample surface 1b to be displayed by the display means 55. Since as is the case with the display means employed in the analyzing apparatus according to the fourth embodiment the display means 55 of a kind having a touch panel on a screen 55b thereof, the operator can specify and input the minute target area by applying a pen tip directly to an arbitrarily chosen position of the image of the sample surface 1b displayed on the screen 55b.

When specification and inputting of the measurement conditions terminate, the sample holder 44 containing the sample 1 is placed at a central portion of the sample support 2. After a start command descriptive of the start of setting and measurement of a minute target area of the sample 1 is inputted, the control means 72 causes the rθ stage 70 to rotate the sample support 2 and a reflection type sensor 110 to detect the projection 44a of the sample holder 44, so that the sample 1 can be oriented in the predetermined direction (that is, a direction conforming to the direction in which the sample surface 1b has been imaged) to thereby establish an initial state. Thereafter, as is the case with the analyzing apparatus according to the fourth embodiment of the present invention, the control means 72 calculates an appropriate angle of rotation and/or an appropriate distance of linear movement of the sample 1, that are effected by the rθ stage 70, with the arbitrarily chosen position of the image, so that the rθ stage 70 can be controlled to set the minute target area in position to allow the specified minute target area of the sample 1 to be most radiated by the primary X-ray 3 to emit the fluorescent X-ray 5 and also to allow the emitted fluorescent X-ray 5 to be incident upon the energy dispersive type detecting means 11. It is to be noted that the holder bench 34g may be provided with a rotational angle adjustment (θ stage) and the reflection type sensor 110 so that the control means 72 can perform a process of determining the orientation of the sample 1 during the imaging.

Thus, with the analyzing apparatus according to the fifth embodiment of the present invention, since the minute target area can be specified by looking at the image of the sample surface 1b on the sample support 2 that is directly videoed immediately, the minute target area of the sample 1 can be quickly and accurately determined. Thereafter, the measurement can be performed in a manner similar to that performed with the analyzing apparatus according to the fourth embodiment. Specifically, the wavelength distribution characteristic of the fluorescent X-ray 5 of a relatively low intensity emitted from the target area is examined broadly in a short length of time by means of the energy dispersive detecting means 11 having a relatively high sensitivity, followed by measurement of the intensity of the fluorescent X-ray over the necessary or desired wavelength range with the use of the wavelength dispersive detecting means 6 having a high resolving power. Accordingly, a quick and accurate analysis is possible with respect to the minute target area of the sample once chosen. In other words, the arbitrarily chosen minute target area of the sample 1 can be quickly and accurately determined and the analysis of the minute target area so determined can be performed quickly and accurately. Therefore, a quick and accurate analysis of the arbitrarily chosen minute target area of the sample 1 can be performed.

Figure 10:
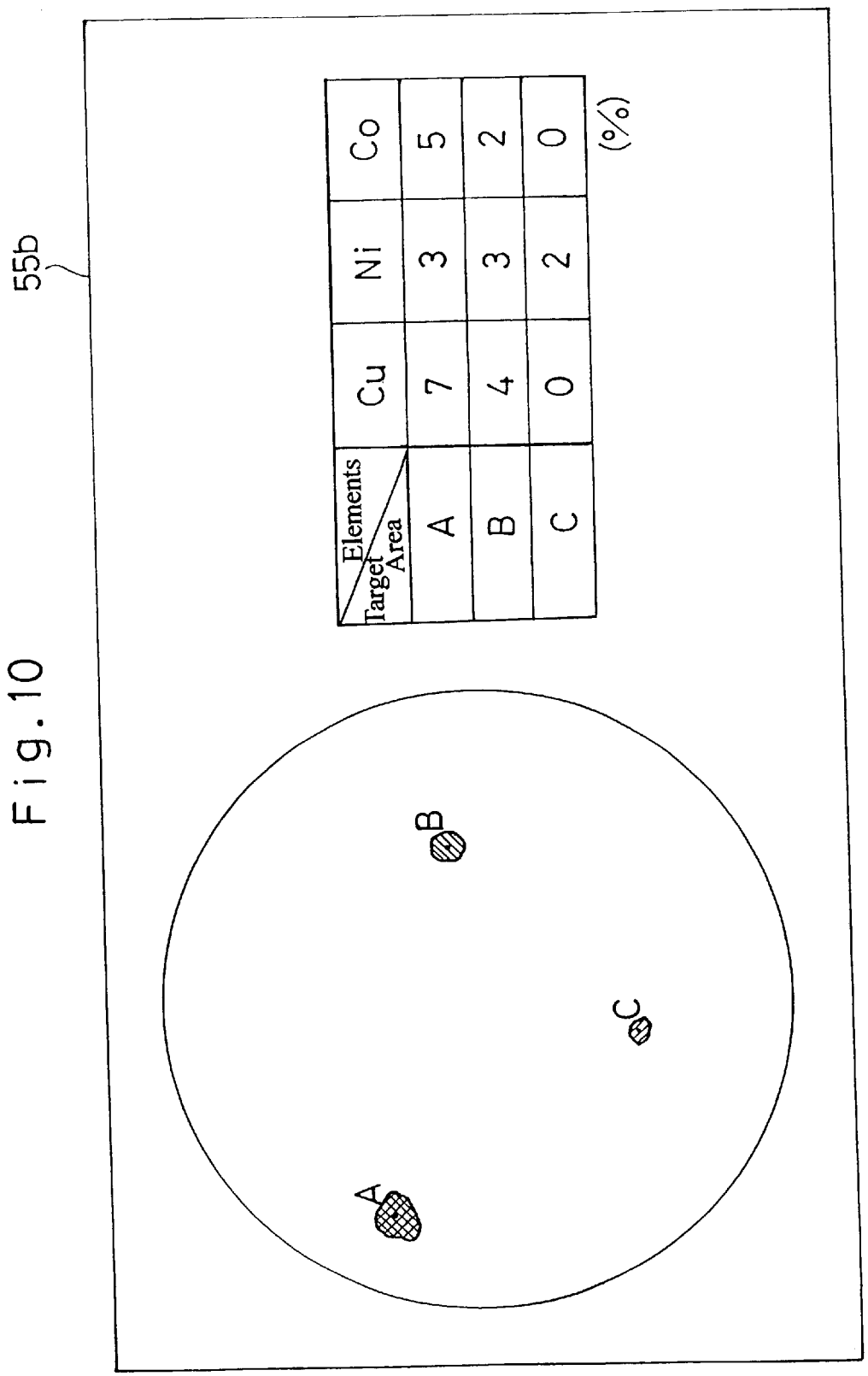
FIG. 10 is a diagram showing one example of a display showing a result of measurement given by the fluorescent X-ray analyzing apparatus according to the fourth or fifth embodiment of the present invention.
Figure 11:
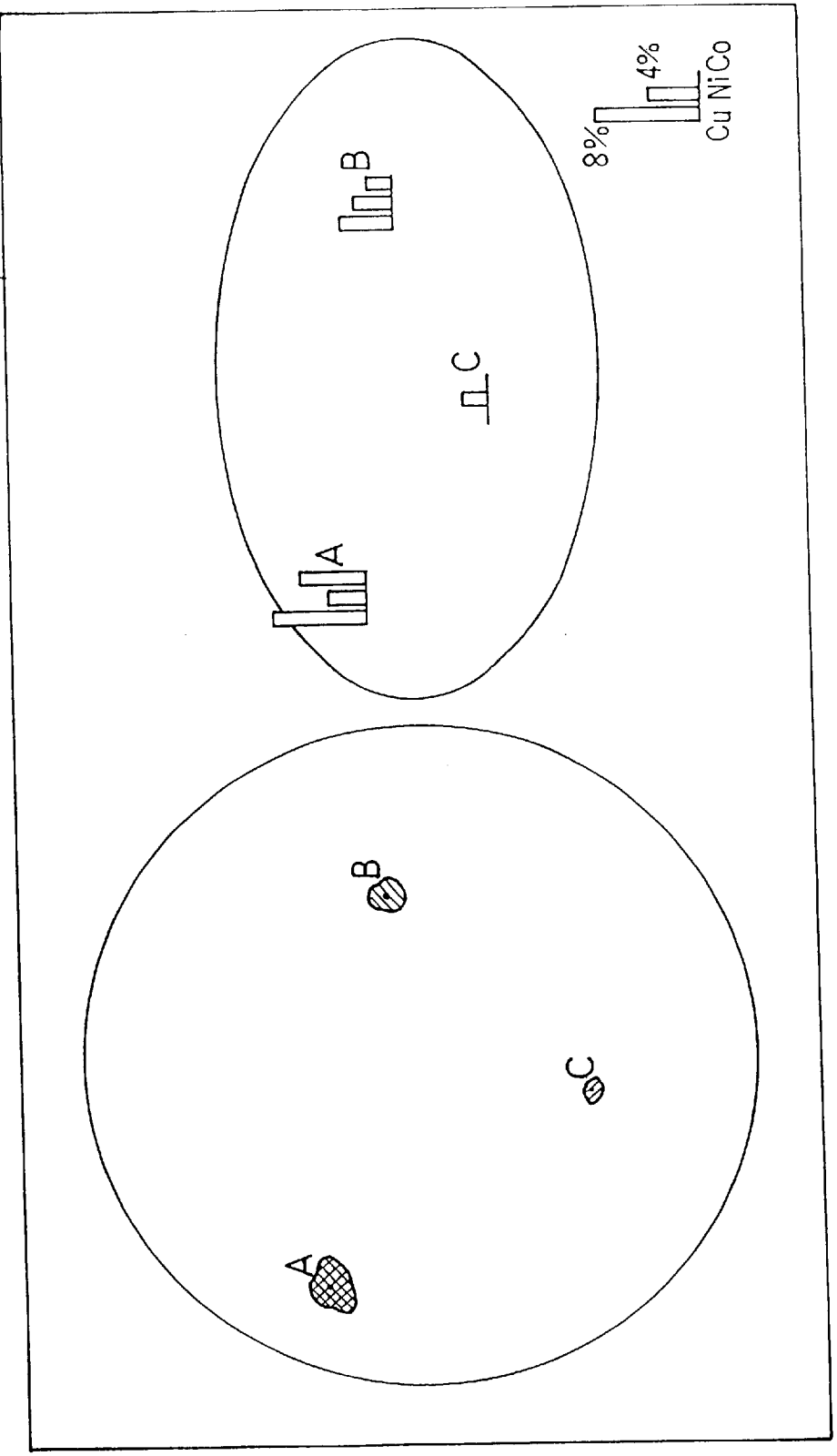
FIG. 11 is a diagram showing another example of the display showing the result of measurement given by the same apparatus.
Figure 12:
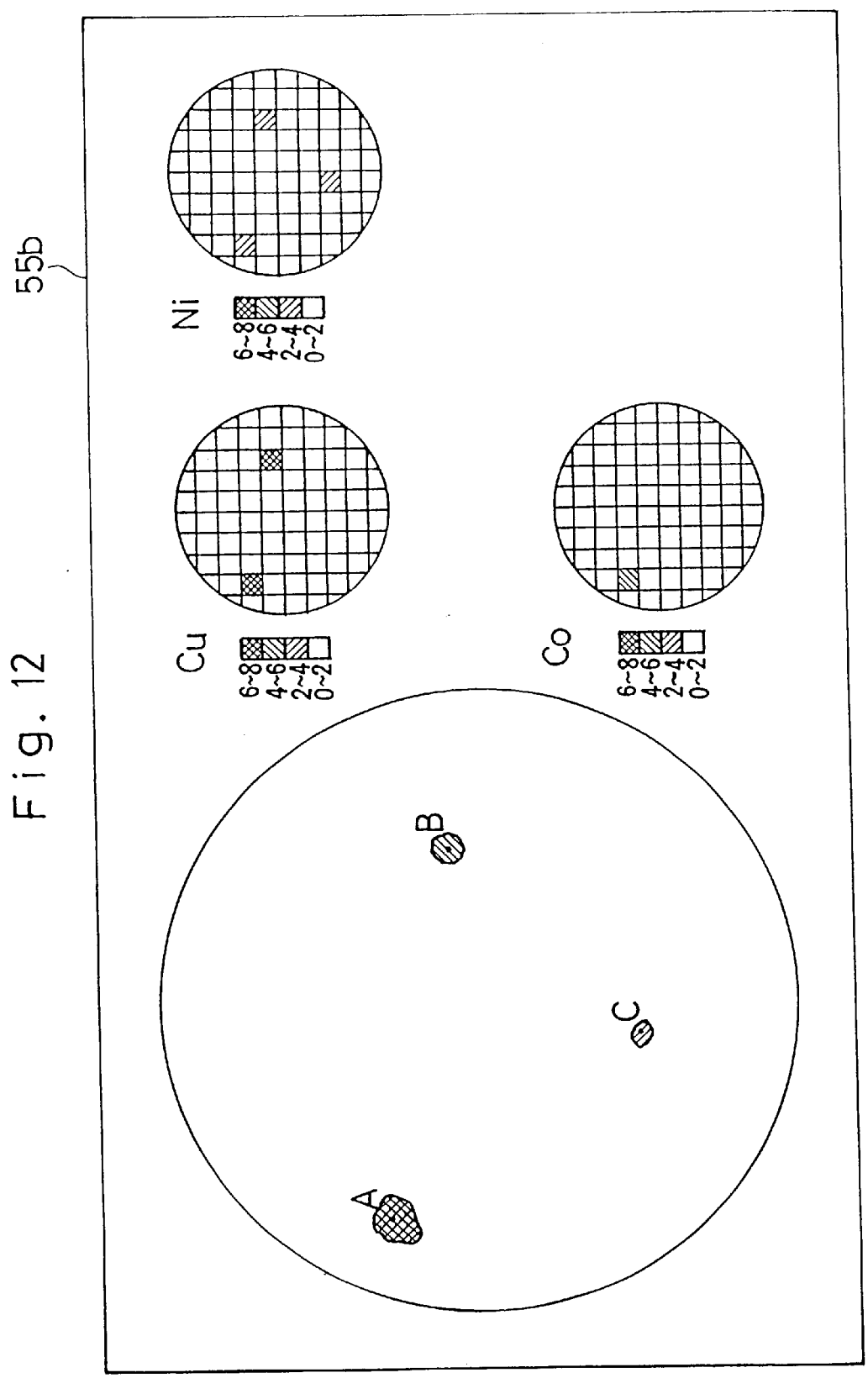
FIG. 12 is a diagram showing a further example of the display showing the result of measurement given by the same apparatus.

In the analyzing apparatus according to the foregoing fifth embodiment of the present invention, since the imaging means 34 is disposed externally of, and not internally of the sample chamber 17 and the spectral analyzing chamber 18 each having a limited space, the analyzing apparatus can be simplified in structure. In other words, no design choice is needed to dispose at least a portion of the imaging means 34 within the sample chamber 17 or the spectral analyzing chamber 18 without allowing the CCD 34a to the vacuum atmosphere.

Where the analyzing apparatus according to any one of the fourth and fifth embodiments of the present invention is utilized, the result of measurement can readily and quickly grasped since the result of measurement can be displayed on the screen 55b of the display means 55 together with the image of the sample surface 1b that has been videoed. By way of example, in FIG. 10, respective positions A, B and C of the target areas specified in the image of the videoed sample surface 1b are displayed in a left-hand portion of the screen 55b in overlapping relation with the image of the sample surface 1b and respective compositions measured at the target areas are displayed in the form of a table in a right-hand portion of the screen 55b. In FIG. 11, while the left-hand portion of the screen 55b provides a visual representation of the respective positions A, B and C of the target areas in a manner similar to that shown in FIG. 10, the right-hand portion of the screen 55b provides a visual representation of the respective compositions measured at the target areas in the form of associated graphic bars. In FIG. 12, while the left-hand portion of the screen 55b provides a visual representation of the respective positions A, B and C of the target areas in a manner similar to that shown in FIG. 10, the right-hand portion of the screen 55b provides, for each of the elements of interest in the target areas, a visual representation of an display area that is a downscaled image of the sample surface, in which area the measured content of the corresponding element of interest appears in terms of the different densities of color, plotted at positions corresponding to the positions of the target areas on the sample surface (In FIG. 12, the different densities of color are conveniently expressed by different hatchings), together with an index bar descriptive of the different densities of color against associated content range. In the visual representation shown in FIG. 12, a numerical range showing, for example, 0~2 speaks that the content is equal to 0 or greater and less than 2%.

It is to be noted that with the analyzing apparatus according to the fifth embodiment of the present invention, the videoed image of the sample surface 1b itself is displayed in a two-dimensional representation as FIG. 9 makes it clear and that with the analyzing apparatus according to the fourth embodiment of the present invention, the videoed image of the sample surface 1*b* is displayed in a perspective representation. It is however preferred that in the analyzing apparatus according to the fourth embodiment, the use is made of an image processing in the display means 55 in combination with the lens 54*b* (FIG. 7) of the imaging means 54 to enable the videoed image of the sample surface to be displayed in a two-dimensional representation for the convenience of the operator. Accordingly, FIGS. 10 to 12 illustrate the screen 55*b* of the display means 55 employed in the analyzing apparatus according to the fourth or fifth embodiment of the present invention.

The analyzing apparatus according to any one of the fourth and fifth embodiments of the present invention is not always limited for use with measurement of the very minute target area, but can be utilized for measurement of target area that are not specifically minute (i.e., the sample in its entirety where it is not specifically minute) if the first collimator 30 shown in FIG. 3 is provided with the throttle apertures of a large size. In such modification, if the fluorescent X-ray 5 emitted from the target area of the sample 1 has a sufficient intensity, the wavelength dispersive type detecting means 6 can be utilized from the beginning to measure such intensity can be measured over a large wavelength range with no need to use the energy dispersive type detecting means 11.

Figure 14:
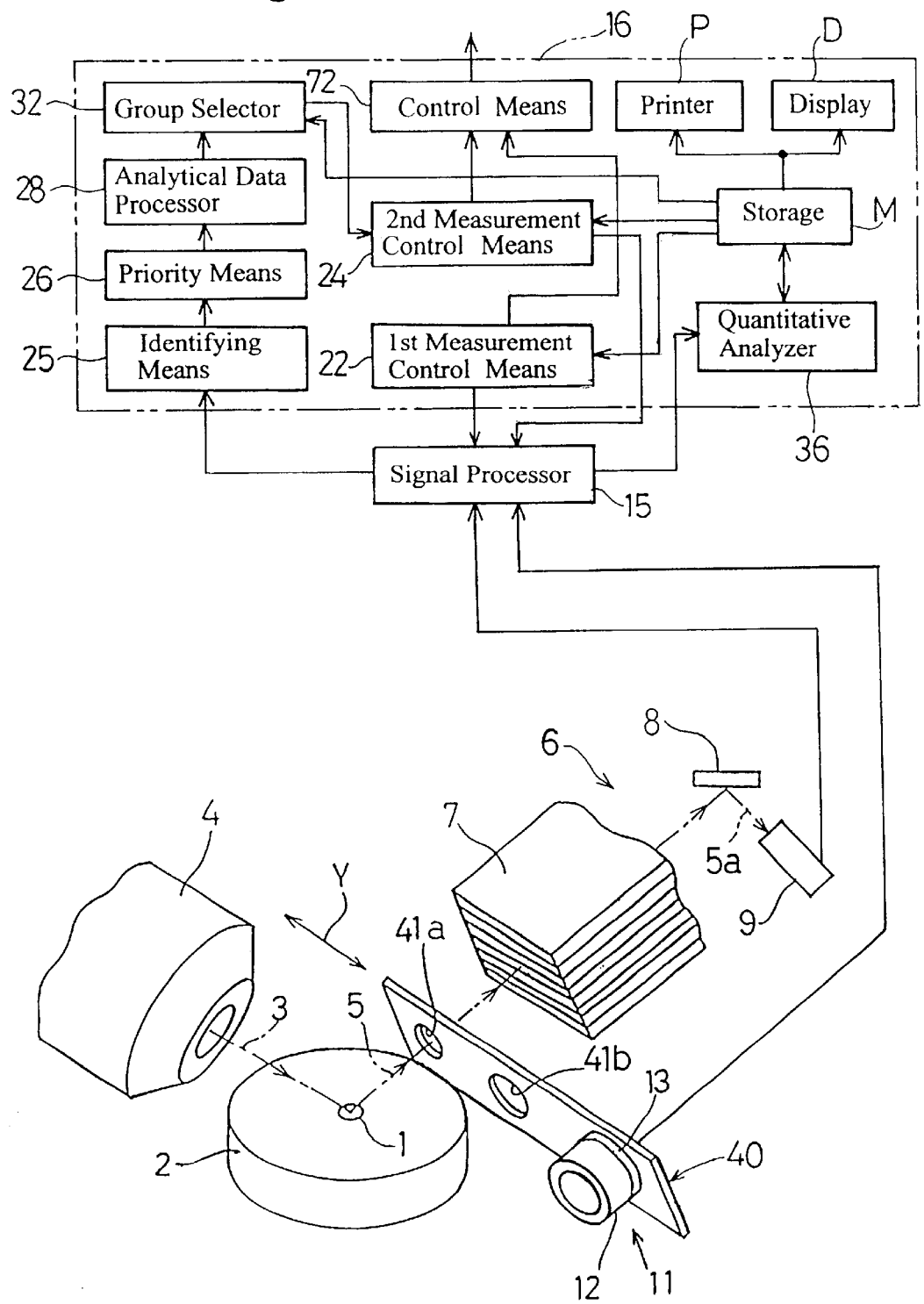
FIG. 14 is a diagram showing the fluorescent X-ray analyzing apparatus according to a sixth preferred embodiment of the present invention.

Referring now to FIG. 14, the analyzing apparatus according to a sixth preferred embodiment of the present invention will be described.

As shown in FIG. 14, the analyzing apparatus according to this embodiment includes a signal processing circuit 15 for processing electric signals representative of the fluorescent X-rays 5*a* detected by the first detector 9 and the fluorescent X-ray 5 detected by the SSD 12, respectively, and a controller 16 controlling the analyzing apparatus in its entirety. The controller 16 includes first and second measurement control means 22 and 24, an identifying means 25, a priority means 26, an analytical data processing means 28, a group selecting means 32, the previously described control means 72 and a quantitative analyzing means 36, all of which are incorporated in a computer (CPU). The controller 16 also includes a storage means (memory) M for storing various data and calibration curve formulas, a display unit D for displaying various contents of operation and various data, and a printer means P for making a print of the contents displayed on the screen. The analyzing apparatus shown in FIG. 14 does not make use of the first collimator 30 and a combination of the rack 61, the stepper motor 63 and the pinion 62 (See FIG. 2) used to drive the first collimator 30. However, other structural features are similar to those employed in the analyzing apparatus according to the second embodiment of the present invention.

The first measurement control means 22 is operable to open a shutter (not shown) of the X-ray source 4 to allow the sample 1 to be radiated by the primary X-ray 3 from the X-ray source 4 and also to measure the intensity of the fluorescent X-ray emitted from an element of interest contained in the sample 1 to thereby provide a first result of measurement. In the case of the wavelength dispersive type detecting means 6, the wavelength to be detected is continuously changed by a scanning mechanism such as, for example, a Goniometer, and the signal processing circuit 15 is controlled to allow the number of pulses outputted from the first detector 9 to be counted so that the intensity of the fluorescent X-ray 5*a* in a region of a light element emitted from the sample 1. In the case of the energy dispersive type detecting means 11, the signal processing circuit 15 is controlled to allow the number of pulses outputted from the SSD 12 to be counted so that the intensity of the fluorescent X-ray 5 mainly in a region of a heavy element emitted from the sample 1.

The identifying means 25 is operable to detect and identify the peak wavelength of the element of interest based on the measured data on the respective intensities of the fluorescent X-rays 5 and 5*a*, so that the kind of the element contained in the sample 1 can be determined. The priority means 26 is operable, where the result of measurement of the fluorescent X-ray 5*a* given by the wavelength dispersive type detecting means 6 indicates overlap of high-order lines and other fluorescent X-rays, to instruct to use the result of measurement of the fluorescent X-ray 5 given by the energy dispersive type detecting means 11. Where no overlap is found, both of the results of measurement are utilized in the form as presented. The overlap in the result of measurement of the fluorescent X-ray 5*a* can be readily found by inferring overlap of the high-order lines from the type of the element obtained. The analytical data processing means 28 performs at least one of the qualitative analysis, the semiquantitative analysis and the quantitative analysis of the sample 1 based on the first result of measurement. Generally the analytical date processing means 28 performs at least the qualitative analysis. A result of the semiquantitative analysis can be used in grouping for the subsequent quantitative analysis.

The group selecting means 32 is operable to select a group to which the sample 1 belongs, from a result of the qualitative analysis or the semiquantitative analysis of the sample 1 that is determined by the analytical data processing means 28. The second measurement control means 24 is operable to determine measurement conditions including an element of interest to be measured and the measurement time during which the measurement is carried out according to the group, drive the scanning mechanism for the wavelength dispersive type detecting means 6 to select and analyze only the wavelength emitted from the element of interest by means of the spectroscope 8, and controls the signal processing circuit 15 so that under the defined measurement conditions the number of the pulses outputted from the first detector 9 can be counted for the measurement time to thereby measure the intensity of the fluorescent X-ray 5*a* to provide a second result of measurement. Where there is an overlap in the result of measurement of the fluorescent X-ray 5*a* given by the wavelength dispersive type detecting means 6 during the semiquantitative analysis, the energy dispersive type detecting means 11 measures the fluorescent X-ray under the measurement conditions similarly determined according to the group, the result of measurement by the energy dispersive type detecting means 11 being preferentially utilized. The quantitative analyzing means 36 is operable to determine, from the second result of measurement of the element of interest obtained in the manner described above, the quantitatively analyzed value of the sample 1.

Figure 15:
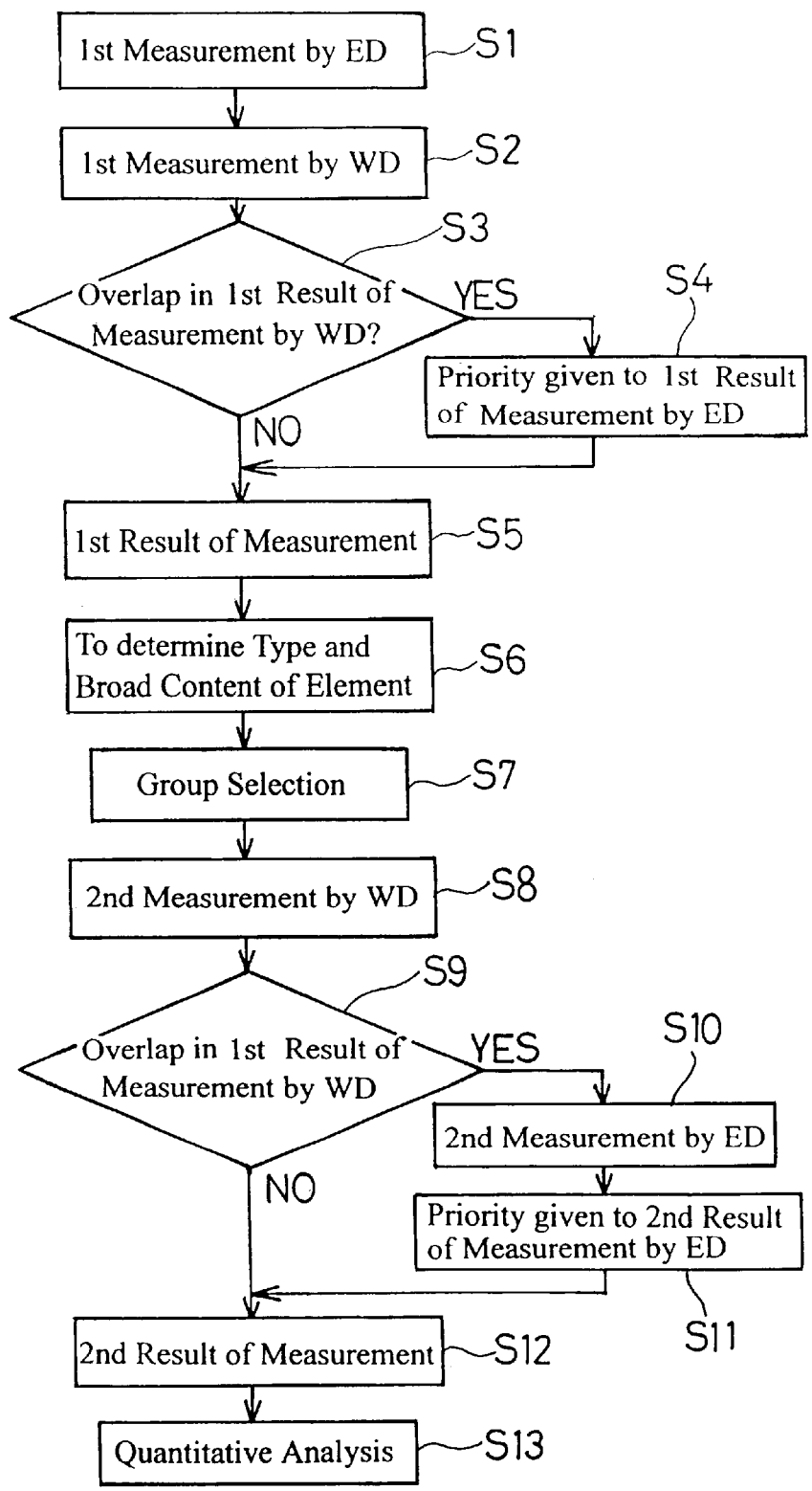
FIG. 15 is a flowchart showing the sequence of operation of the fluorescent X-ray analyzing apparatus shown in FIG. 14.
Figure 16:
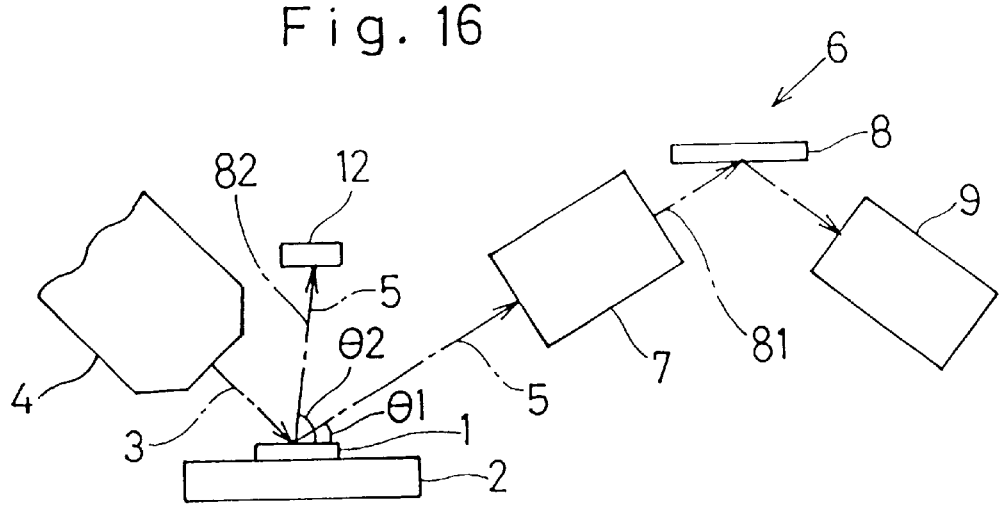
FIG. 16 is a schematic side view of the first prior art fluorescent X-ray analyzing apparatus.
Figure 17:
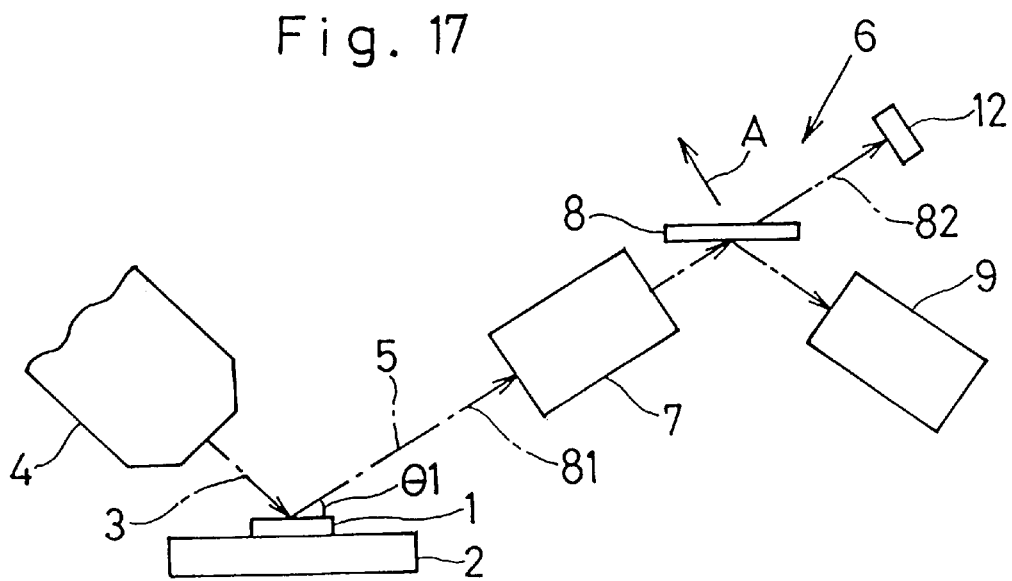
FIG. 17 is a schematic side view of the second prior art fluorescent X-ray analyzing apparatus.

The sequence of operation of the fluorescent X-ray analyzing apparatus of the structure described above in accordance with the sixth embodiment of the present invention will now be described with reference to the flowchart shown in FIG. 15.

(1) First Measurement:

The first measurement control means 22 shown in FIG. 14 is first activated and the collimator 40 is driven by the control means 72 to bring the SSD (semiconductor detector) 12 of the energy dispersive type detecting means (ED detecting means) 11 into alignment with the path of travel of the fluorescent X-ray 5. Then, by instruction from the first measurement control means 22, the signal processing circuit 15 counts the number of the pulses outputted from the SSD 12 during a relatively short length of measurement time to thereby analyze the intensity of the fluorescent X-ray 5 mainly in the region of the heavy element emitted from the sample 1 (Step S1 in FIG. 15). Based on the intensity given by the first measurement done by the ED detecting means, the identifying means 25 detects and identifies the peak wavelength of the element of interest. During the first measurement performed by the ED detecting means, although the SSD 12 has a low detection sensitivity with respect to the element in the region of the light element, broad measurement of the intensity of the fluorescent X-ray in the region of the light element results in identification of the type of the light element contained in the sample 1 to a certain extent.

Thereafter, the first measurement control means 22 is activated and the collimator 40 is driven by the control means 72 to bring one of the throttling apertures 40a and 40b of the wavelength dispersive type detecting means (WD detecting means), that is appropriate to the size of the shape of the target area of the sample 1, into alignment with the path of travel of the fluorescent X-ray 5. Then, by instruction from the first measurement control means 22, while the scanning mechanism scans a region of the light element, the signal processing circuit 15 counts the number of pulses outputted from the first detector 9 in a length of measurement time that is shorter than that required during the standard quantitative analysis, to thereby measure the intensity of the fluorescent X-ray 5 in the region of the light element emitted from the sample 1 (Step S3). The first measurement performed by this WD detecting means is carried out only to the region of the light element and, therefore, the length of time required to accomplish the measurement will not be so long.

It is to be noted that where the type of the light element contained in the sample 1 is known beforehand, only the first measurement by the WD detecting means may be performed with respect to such light element and that the measurement of the light element by the first measurement done by the WD detecting means may be followed by measurement of the heavy element region by the first measurement done by the ED detecting means.

Should measurement be difficult to accomplish because in the first result of measurement done by the WD detecting means with respect to the light element, for example, one spectrum of the intensity of the light element is overlapped with high-order lines of other elements, the priority means 26 preferentially choose the first result of measurement done by the ED detecting means at step S4. Since no high-order line is measured by the SSD 12, giving priority to the first result of measurement by the ED detecting means makes it possible to accomplish a further highly accurate measurement. Where no overlap is found, both of the results of measurement are utilized in the form as presented to secure the first result of measurement at step S5.

Then, by the operation of the analytical data processing means 28, the type of and an approximate value of the content of the elements contained in the sample 1 are determined, thereby completing the semiquantitative analysis at step S6. In this way, the region of the light element can be measured by the wavelength dispersive type detecting means 6 with high accuracy and mainly the region of the heavy element can be measured in a short length of time by the energy dispersive type detecting means 11. Therefore, the semiquantitative analysis to determine the type of and the approximate content of the elements contained in the sample 1 can be accomplished in a short length of time with high accuracy, that is, quickly and accurately.

(2) Group Selection:

The memory M stores, as conditions used to classify the types of the samples 1 into groups, the types of and the contents of the elements for each group. The group selecting means 32 checks the type of and the approximate content of the element contained in the sample 1, that are given by the semiquantitative analysis, against the group classifying conditions stored in the memory M to thereby automatically select the group to which the sample 1 belongs, for example, stainless steel, iron ore, cement and so on, at step S7. Should a variation occur in the measured value of the intensity of the fluorescent X-ray, only the peak intensity of the element of interest is apt to result in an erroneous determination of the sample 1 and, therefore, based on not only the peak intensity of the element of interest, but also the approximate content of the element of interest, the group is selected. Therefore, the erroneous determination of the type of the sample 1 can advantageously be minimized.

It is to be noted that where no overlap of the fluorescent X-ray 5a such as the high-order line occurs in the first result of measurement given by the WD detecting means, the use of the priority means 26 may be dispensed with.

Also, where the variation in measured value of the intensity of the fluorescent X-ray can be negligible, or where the group classification may be rough, the group may be selected according to only the type of the element of interest contained in the sample 1.

(3) Quantitative Analysis:

Finally, the second measurement control means 24 reads out from the memory M such measurement conditions appropriate to the selected group as, for example, the power of the X-ray source 4, the X-ray radiating time, the length of time (measurement time) during which the number of pulses of the signal processing circuit 15 is counted, to control the X-ray source 4, the scanning mechanism and the signal processing circuit 15 so that during each measurement time with respect to each of the elements of interest, the number of pulses outputted from the first detector 9 of the wavelength dispersive type detecting means 6 can be counted to measure the peak intensity of each element of interest at step S8 (second measurement by the WD detecting means). Where no overlap occur in the first result of measurement by the WD detecting means during the semiquantitative analysis at step S3 (Step S9), the result of this second measurement is utilized in the form as presented to give a second result of measurement at step S12. It is to be noted that in such case, instead of the result of the second measurement by the WD detecting means, a result of the second measurement by the ED detecting means as will be described later may be employed.

At step S9, where the overlap occurs in the first result of measurement by the WD detecting means during the semi-quantitative analysis at step S3, the second measurement by the ED detecting means for measuring the fluorescent X-ray 5 is carried out at step S10 by the energy dispersive type detecting means 11 under the measurement condition set up according to the selected group, the result of which is subsequently preferentially utilized at step S11 to give a second result of measurement at step S12.

Thereafter, the quantitative analyzing means 36 makes use of the second result of measurement to determine the quantitatively analyzed value of the sample 1. In other words, the content in the sample 1 is determined at step S13 from the peak intensity of each of the elements of interest measured, by the utilization of a fundamental parameter method or a calibration curve method in which calibration curve formulas appropriate to the types of the elements contained in the sample 1 that are stored in the memory M are utilized.

The result of the quantitative analysis is, after having been temporarily stored in the memory M, displayed by the display unit D and/or printed by the printer means P. In this way, by performing the measurement based on the measurement conditions appropriate to the group, the quantitative analysis can be carried out in a short length of time with high accuracy, that is, quickly and accurately.

Where the sample 1 is a thin film formed on a substrate, in place of the approximate contents of elements, the approximate value of the amount of deposit of and the film thickness of the thin film on the substrate may be determined during the first measurement and, after the group selection, the amount of deposit of and the film thickness of the thin film may be determined as qualitatively analyzed values.

It is to be noted that as hereinbefore discussed, the qualitative analysis of the sample 1 may be carried out base don the first result of measurement in which the intensity of the fluorescent X-ray mainly in the region of the light element is measured by the wavelength dispersive type detecting means (WD detecting means) 6 and the intensity of the fluorescent X-ray mainly in the region of the heavy element is measured by the energy dispersive type detecting means (ED detecting means) 11.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A fluorescent X-ray analyzing apparatus which comprises:
    detecting means for detecting and analyzing, by means of a detecting means, fluorescent X-ray emitted from at least one predetermined target area of a sample to be analyzed as a result of excitation of such target area with a primary X-ray;
    said detecting means comprising a wavelength dispersive type detecting means including a spectroscope and a first detector, and an energy dispersive type detecting means including a second detector of an energy dispersive type; and
    wherein an angle formed between a first path of travel of the fluorescent X-ray from the target area towards the spectroscope and a surface of the sample is equal to an angle formed between a second path of travel of the fluorescent X-ray from the target area towards the second detector of the energy dispersive type and a surface of the sample, but said second path of travel of the fluorescent X-ray is shorter than said first path of travel of the fluorescent X-ray.

2. The fluorescent X-ray analyzing apparatus as claimed in claim 1, further comprising a detector drive mechanism for selectively advancing and retracting the second detector of the energy dispersive type into and out of alignment with the first path of travel of the fluorescent X-ray, and wherein said first and second paths of travel of the fluorescent X-ray lie on the same axis when the second detector of the energy dispersive type is advanced by said detector drive mechanism.

3. The fluorescent X-ray analyzing apparatus as claimed in claim 2, further comprising a first collimator positioned between the second detector of the energy dispersive type and the sample and having at least one throttling aperture defined therein for passage of the fluorescent X-ray therethrough, the fluorescent X-ray passing through the throttling aperture in the first collimator being detected by the second detector of the energy dispersive type or detected by the first detector after having been analyzed by the spectroscope.

4. The fluorescent X-ray analyzing apparatus as claimed in claim 3, further comprising a second collimator disposed between the first collimator and the spectroscope and having at least one throttle aperture defined therein, and wherein said second detector of the energy dispersive type is fitted to the second collimator.

5. The fluorescent X-ray analyzing apparatus as claimed in claim 1, further comprising a sample drive mechanism for moving the target area of the sample placed on a sample support.

6. The fluorescent X-ray analyzing apparatus as claimed in claim 1, wherein said spectroscope is a double crystal spectroscope including two spectroscopic crystals positioned fore and aft along the path of travel of the fluorescent X-ray.

7. The fluorescent X-ray analyzing apparatus as claimed in claim 3, further comprising:
    a sample drive mechanism for moving the target area of the sample placed on a sample support;
    imaging means of imaging the surface of the sample to form a sample image;
    display means for displaying the sample image formed by the imaging means; and
    control means for controlling the sample drive mechanism so as to allow the fluorescent X-ray, emitted from a site of the sample, specified with reference to the sample image displayed by the display means, to be incident upon any of the wavelength dispersive type detecting means and the energy dispersive type detecting means.

8. The fluorescent X-ray analyzing apparatus as claimed in claim 7, wherein said imaging means images the surface of the sample placed on the sample support to form the sample image.

9. The fluorescent X-ray analyzing apparatus as claimed in claim 8, wherein said wavelength dispersive type detecting means includes a Soller slit, and said Soller slit and at least a portion of the imaging means are positioned between the first collimator and the spectroscope, and further comprising a selector means for bringing one of them selectively to a position confronting the sample placed on the sample support.

10. The fluorescent X-ray analyzing apparatus as claimed in claim 4, further comprising:
    a sample drive mechanism for moving the target area of the sample placed on a sample support;
    imaging means of imaging the surface of the sample to form a sample image;
    display means for displaying the sample image formed by the imaging means; and
    control means for controlling the sample drive mechanism so as to allow the fluorescent X-ray, emitted from a site of the sample, specified with reference to the sample image displayed by the display means, to be incident upon any of the wavelength dispersive type detecting means and the energy dispersive type detecting means.

11. The fluorescent X-ray analyzing apparatus as claimed in claim 10, wherein said imaging means images the surface of the sample placed on the sample support to form the sample image.

12. The fluorescent X-ray analyzing apparatus as claimed in claim 11, wherein said wavelength dispersive type detecting means includes a Soller slit, and said Soller slit and at least a portion of the imaging means are positioned between the first collimator and the spectroscope, and further comprising a selector means for bringing one of them selectively to a position confronting the sample placed on the sample support.

13. A fluorescent X-ray analyzing apparatus which comprises:

detecting means for detecting and analyzing, by means of a detecting means, fluorescent X-ray emitted from at least one predetermined target area of a sample to be analyzed as a result of excitation of such target area with a primary X-ray;

said detecting means comprising a wavelength dispersive type detecting means including a spectroscope and a first detector, and an energy dispersive type detecting means including a second detector of an energy dispersive type;

a first measurement control means for obtaining a first result of measurement by causing the wavelength dispersive type detecting means to measure mainly an intensity of fluorescent X-rays in a region of a light element and also causing the energy dispersive type detecting means to measure mainly an intensity of fluorescent X-rays in a region of a heavy element; and an analytical data processing means for performing at least one of qualitative analysis, semiquantitative analysis and quantitative analysis of the sample based on the first result of measurement.

14. The fluorescent X-ray analyzing apparatus as claimed in claim 13, further comprising a priority means for preferentially utilizing a result of measurement by the energy dispersive type detecting means as the first result of measurement in the event that a spectrum measured by the wavelength dispersive type detecting means contain an overlap of high-order lines.

15. The fluorescent X-ray analyzing apparatus as claimed in claim 13, further comprising:

a group selecting means for selecting a group to which the sample belongs, from a result of one of the qualitative analysis and the semiquantitative analysis of the sample determined by the analytical data processing means;

a second measurement control means for setting measurement conditions, including elements to be measured, according to the group and for giving a second result of measurement by measuring the intensity of the fluorescent X-ray under the measurement conditions thus set; and a quantitative analysis means for determining a quantitatively analyzed value of the sample from the second result of measurement obtained by the second measurement control means with respect to the elements to be measured.

* * * * *